US010555536B2

(12) United States Patent
Sawant

(10) Patent No.: US 10,555,536 B2
(45) **Date of Patent: *Feb. 11, 2020**

(54) CROP FORTIFICATION, NUTRITION AND CROP PROTECTION COMPOSITION

(71) Applicant: Arun Vitthal Sawant, Maharashtra (IN)

(72) Inventor: Arun Vitthal Sawant, Maharashtra (IN)

( * ) Notice: Subject to any disclaimer, the term of this patent is extended or adjusted under 35 U.S.C. 154(b) by 0 days.

This patent is subject to a terminal disclaimer.

(21) Appl. No.: 16/047,834

(22) Filed: Jul. 27, 2018

(65) Prior Publication Data

US 2019/0029266 A1 Jan. 31, 2019

(30) Foreign Application Priority Data

Jul. 27, 2017 (IN) ............................ 201721026745

(51) Int. Cl.
*A01N 63/04* (2006.01)
*A01N 65/03* (2009.01)
(Continued)

(52) U.S. Cl.
CPC ............ *A01N 63/04* (2013.01); *A01N 25/12* (2013.01); *A01N 63/00* (2013.01); *A01N 65/03* (2013.01);
(Continued)

(58) Field of Classification Search
CPC ........ A01N 25/12; A01N 65/03; A01N 25/14; A01N 63/00; A01N 63/04; C05G 3/0058; C05G 3/02; C05D 9/00
See application file for complete search history.

(56) References Cited

U.S. PATENT DOCUMENTS 4,774,186 A 9/1988 Schaefer, Jr. et al.
7,638,506 B2 * 12/2009 Ozaki .................. A01N 25/12 424/405

(Continued)

FOREIGN PATENT DOCUMENTS

| | | | |
|---|---|---|---|
| CN | 101555177 | A | 10/2009 |
| CN | 102229515 | B | 11/2013 |
| WO | 2011031287 | A2 | 3/2011 |

OTHER PUBLICATIONS

Written Opinion for International Application No. PCT/IB2018/055632.

(Continued)

*Primary Examiner* — Carlos A Azpuru
(74) *Attorney, Agent, or Firm* — Ladas & Parry LLP

(57) ABSTRACT

The invention relates to an algal granular composition. More particularly, the invention relates to an algal granular composition comprising at least one alga, and at least one agrochemically acceptable excipients selected from one or more of surfactants, binders or disintegrant having weight ratio of algae to at least one of surfactant, binder or disintegrant in the range of 99:1 to 1:99. The algae comprise 0.1% to 90% by weight of the total composition. The composition has a particle size in the range of 0.1 microns to 60 microns. Furthermore, the invention relates to a process of preparing the algal granular composition comprising at least one alga and at least one agrochemically acceptable excipient. The invention further relates to a method of treating the plants, seeds, crops, plant propagation material, locus, parts thereof or the soil with the algal granular composition.

17 Claims, 1 Drawing Sheet

Figure 1:
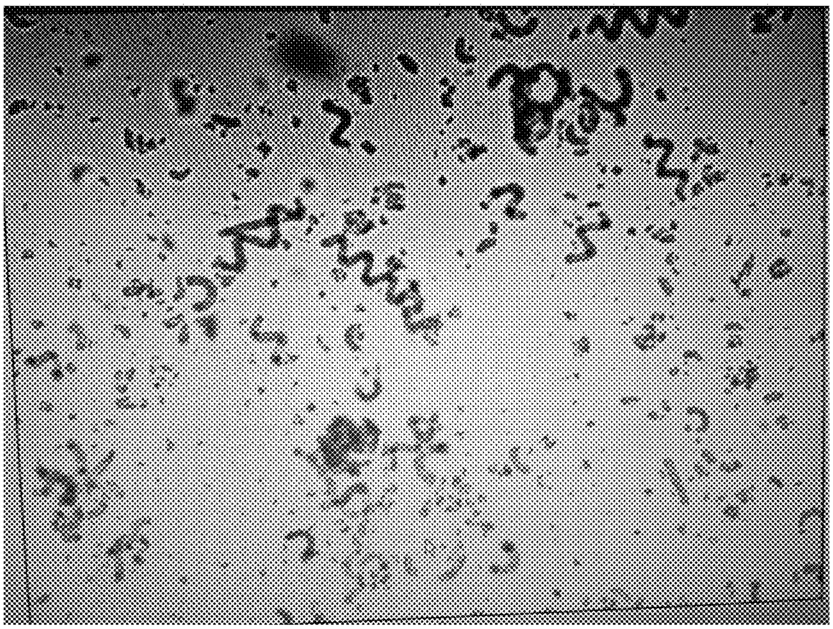

(51) Int. Cl.

| | |
|---|---|
| ***C05G 3/00*** | (2006.01) |
| ***C05G 3/06*** | (2006.01) |
| ***A01N 25/12*** | (2006.01) |
| ***A01N 63/00*** | (2006.01) |
| ***C05C 9/00*** | (2006.01) |
| ***C05D 9/00*** | (2006.01) |
| ***C05F 11/00*** | (2006.01) |
| ***C05G 3/02*** | (2006.01) |

(52) U.S. Cl.

CPC .................. *C05C 9/00* (2013.01); *C05D 9/00* (2013.01); *C05F 11/00* (2013.01); *C05G 3/007* (2013.01); *C05G 3/02* (2013.01); *C05G 3/06* (2013.01)

(56) References Cited

U.S. PATENT DOCUMENTS 7,829,499 B2 * 11/2010 Yamashita ............. A01N 25/12
424/489
8,273,685 B2 * 9/2012 Dairiki ................... A01N 25/04
504/124

OTHER PUBLICATIONS

CN 102229515 B _ Espacenet English Abstract.
CN 101555177 A _ Espacenet English Abstract.

* cited by examiner

CROP FORTIFICATION, NUTRITION AND CROP PROTECTION COMPOSITION

1. FIELD OF THE INVENTION

The invention relates to an algal granular composition. More particularly, the invention relates to an algal granular composition comprising at least one alga, and at least one agrochemically acceptable excipient, the composition having excellent dispersibility, suspensibility and flowability. Furthermore, the invention relates to a process of preparing the algal granular composition comprising at least one algae and at least one agrochemically acceptable excipient. The invention further relates to a method of treating the plants, seeds, crops, plant propagation material, locus, parts thereof or the soil with the algal granular composition.

2. BACKGROUND OF THE INVENTION

In describing the embodiments of the invention, specific terminology is chosen for the sake of clarity. However, it is not intended that the invention be limited to the specific terms so selected and it is to be understood that each specific term includes all technical equivalents that operate in a similar manner to accomplish a similar purpose.

Several agrochemical agents are being used at high dosages for long periods of time as fertilizers and for countering pests and diseases. These chemical agents are a constant burden on the environment as they contaminate the soil, water, turf, and other vegetation. In addition to countering pests and diseases, they can be toxic to a host of other organisms including birds, fish, beneficial insects, and non-target plants. Most of the agrochemical agents secrete into soils and groundwater which can end up in drinking water also. The sprays can drift and pollute the air. Further nutrient losses are also a cause for concern due to the economics, as well as due to environmental reasons.

One of the key challenges today is deteriorating soil health. Extensive use of soil fertilizers and pesticides has reduced organic and microbial matter of the soil. Plants are unable to uptake nutrients applied to the soil. Biological materials such as algae, fungi and bacteria are useful alternatives to chemical agents for improvement and/or maintenance of soil nutrients. Algae are useful alternative to the chemical agents for improving the soil and plant health and also to control the pests. Few algal products have been known to be used as fertilizers and plant nutrients in order to decrease the burden on the environment as well as on the health of farmers and consumers. However, their use needs to be optimized and their application needs to be improved in order to provide an economical result in terms of yield, plant growth, vitality and vigor to the farmer and also reduce the burden on the environment.

Prior art documents talk about incorporating algae as a coat over a core granule, but these granules cannot disperse or suspend well and cannot be applied effectively in drip or sprinkler irrigation, as they tend to block the nozzles and this poses a big application challenge in agriculture. Similar is the case with commercially available alga powders where they cannot be used in drip or sprinkler irrigation systems.

Figure 2:
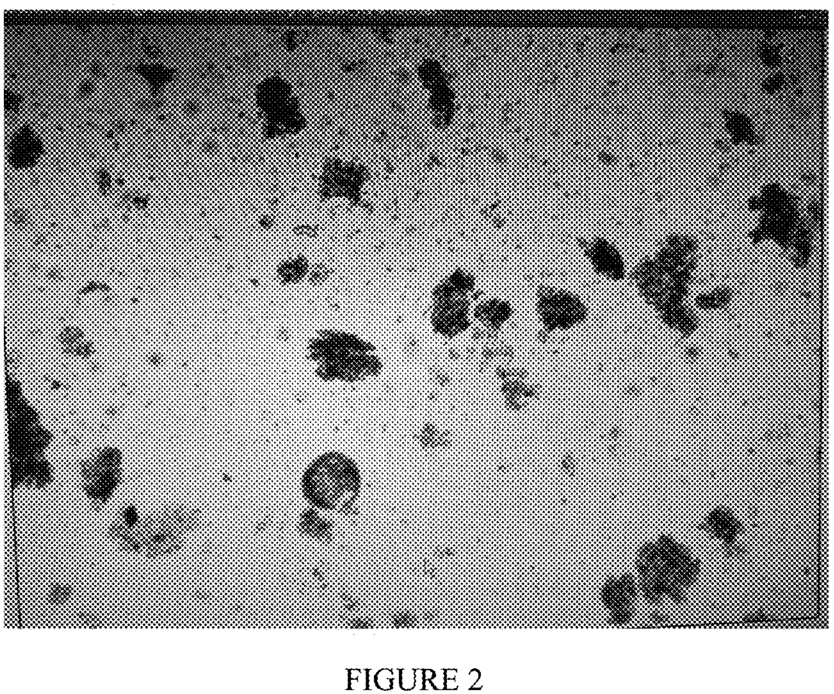

While microbial organisms are generally not viable under high shear, surprisingly the inventors have determined that despite of cells being lysed (as can be seen in FIG. 2), a water dispersible granules of the present invention comprising at least one algae and at least one agrochemically acceptable excipient, with a particle size of 0.1 microns to 60 microns demonstrates excellent field efficacy, for e.g. in the uptake of nutrients from the soil, in the yields and growth of the crops, provides greater prophylactic control over plant pathogenic disease. The water dispersible granules of the present invention also exhibit superior physical characteristics such as suspensibility, dispersibility, flowability and wettability. These superior characteristics of the product results in superior field efficacy without the need of using any chemical products such as urea. The compositions of the present invention also demonstrated superior performance under accelerated storage and also surprisingly be used in drip irrigation.

3. SUMMARY OF THE INVENTION

The invention relates to granular compositions of at least one alga. More particularly, the invention relates to water dispersible granular composition comprising at least one alga and agrochemical excipients including one or more of surfactants, binders or disintegrant wherein the composition exhibits excellent dispersibility, suspensibility, flowability and wettability. The algae comprise 0.1% to 90% by weight of the total composition. The composition includes algae and one or more of surfactants, binders or disintegrant in weight ratio of 99:1 to 1:99 and has a particle size in the range of 0.1 microns to 60 microns. The algae includes one or more of green algae, red algae, golden algae, brown algae, golden-brown algae, blue algae, blue-green algae or their species.

Furthermore, the invention relates to a process of preparing the algal granular composition including at least one alga and at least one agrochemically acceptable excipient. The invention further relates to a method of treating the plants, seeds, crops, plant propagation material, locus, parts thereof or the soil with the algal granular composition.

According to an embodiment, the invention can further relate to the use of the algal granular composition as at least one of a nutrient composition, a plant strengthener composition, a soil conditioner composition, plant fortification, plant protection and a yield enhancer composition.

According to an embodiment, the invention further relates to a method of improving the plant health, improving the plant nutrition, fortifying the plant, protecting the plant, enhancing the plant yield, strengthening the plant or conditioning the soil; the method comprising treating at least one of seeds, seedling, crops, a plant, plant propagation material, locus, parts thereof or to the surrounding soil with effective amount of the algal granular composition involving at least one algae and at least one agrochemically acceptable excipient.

It was also observed that the composition exhibited good physical and chemical properties, good release properties, enhanced stability even at extended storage under higher temperatures which in turn results in superior field performance.

4. BRIEF DESCRIPTION OF THE DRAWINGS

For a more complete understanding of the invention reference should now be made to the embodiments illustrated in greater detail in the accompanying drawings and described by way of embodiments of the invention.

FIG. 1: Illustrates a microscopic image of the pure spirulina powder at 10× magnification. The image depicts typical intact spiral cells and lysed cells of *Spirulina* together.

FIG. 2: Illustrates a microscopic image of the spirulina (50%) water dispersible granules prepared as per embodiment of the invention at 10× magnification. The image depicts lysed cells of *Spirulina.*

5. DESCRIPTION OF THE INVENTION

In describing the embodiment of the invention, specific terminology is chosen for the sake of clarity. However, it is not intended that the invention be limited to the specific terms so selected and it is to be understood that each specific term includes all technical equivalents that operate in a similar manner to accomplish a similar purpose.

The invention relates to an algal granular formulation including at least one alga and at least one agrochemically acceptable excipient whereby the composition exhibits improved dispersibility and suspensibility. According to an embodiment, the granular composition further exhibits improved flowability and wettability.

As used herein the term "granular" composition includes water dispersible granules, particles and grains.

It is well known that microorganisms including bacteria fungie, algae, are not viable when subjected to high shear, and microbial cells tend to get lysed when subjected to shear. FIG. 1. Depicts an image of pure or raw spirulina, which shows a large number of living cells. During preparation of the water dispersible granule composition according to an embodiment of the present invention, the algae undergoes high shear resulting in the lysis of the cell as shown in the FIG. 2. However, despite the fact that the cells are lysed, it is surprisingly observed that the water dispersible granule comprising the algae, according to the current invention, demonstrate excellent efficacy when applied to the seeds, seedling, crops, a plant, plant propagation material, locus, parts thereof or to the surrounding soil.

Surprisingly, the inventors have determined that the composition of the water dispersible granule of the present invention displays enhanced efficacy at reduced dosage of application of the composition as compared to other prior art compositions of algae.

According to an embodiment, the granular composition is a water dispersible granular composition.

When these water dispersible granules come in contact with an aqueous medium, they disperse immediately to release the material, and remain dispersed and suspended uniformly throughout the aqueous medium over a long period of time.

The inventors have further determined that the water dispersible granular composition of the present invention surprisingly has good flowability, which inturn reduces the loss of material while handling the product, at the time of packaging as well as in the field.

According to another embodiment, the algae is microalgae, salt water algae or fresh water algae or species, derivatives or mixtures thereof.

According to further embodiment, the algae is at least one belonging to the group selected from green algae, red algae, golden algae, brown algae, golden-brown algae, blue algae or blue-green algae or their derivatives, species and mixtures thereof.

According to still further embodiment, the algae is at least one selected from the division, but not limited to Cyanobacteria, Ochrophytes, Glaucophytes, Rhodoplasts, Rhodophytes, Chloroplasts, Chrysophyta, Synurophytes, Silicoflagellata, Heterokonts, Crytophytes, Haptophytes, Euglenophytes, Chlorophytes, Charophytes, Land Plants, Embrophyta Or Chlorarachniophytes or their derivatives, species and mixtures thereof. However, those skilled in the art will appreciate that it is possible to utilize any other algae known in the art from other division, without departing from the scope of the invention.

According to further embodiment, the algae is least one selected from the family, but not limited to Bryopsidaceae, Acrotylaceae, Areschougiaceae, Cystocloniaceae, Dicranemataceae, Hypneaceae, Dumontiaceae, Caulerpaceae, Codiaceae, Halimedaceae, Udoteaceae, Anadyomenaceae, Polyphysaceae, Siphonocladaceae, Valoniaceae, Ulvaceae, Chordariaceae, Punctariaceae, Dictyotaceae, Ectocarpaceae, Rhodymeniaceae, Gelidiaceae, Cystoseiraceae, Sargassaceae, Sporochnaceae, Sphacelariaceae, Scytosiphonaceae, Alariaceae, Gracilariaceae, Rhizophyllidaceae, Porphyridiaceae, Acrochaetiaceae, Bonnemaisoniaceae, Ceramiaceae, Dasyaceae, Rhodomelaceae, Delesseriaceae, Phacelocarpaceae, Halymeniaceae, Liagoraceae, Chrysomonadales, Chrysocapsales, Chrysosphaerales, Chrysotrichales, Heterokontae, Diatomeae, Galaxauraceae, Plocamiaceae, Champiaceae, Sebdeniaceae, Lomentariaceae, Peyssonneliaceae, Nizymeniaceae, Kallymeniaceae, Corallinaceae, Nemastomataceae, Prymnesiophycees, Choristocarpaceae, Discosporangiaceae, Petrodermataceae, Syringodermataceae, Onslowiaceae, Dictyotaceae, Lithodermataceae, Eustigmatophyte, Phaeostrophionaceae, Sphacelodermaceae, Stypocaulaceae, Cladostephaceae, Sphacelariaceae, Asterocladaceae, Lessoniaceae, Ascoseiraceae, Cutleriaceae, Arthrocladiaceae, Desmarestiaceae, Acinetosporaceae, Adenocystaceae, Prasinophyceae, Chordariaceae, Chordariopsidaceae, Mesosporaceae, Myrionemataceae, Pylaiellaceae, Bifurcariopsidaceae, Durvillaeaceae, Fucaceae, Himanthaliaceae, Hormosiraceae, Notheiaceae, Sargassaceae, Seirococcaceae, Akkesiphycaceae, Alariaceae, Chordaceae, Costariaceae, Pseudochordaceae, Nemodermataceae, Neoralfsiaceae, Ralfsiaceae, Chnoosporaceae, Splachnidiaceae, Sporochnaceae, Halosiphonaceae, Masonophycaceae, Phyllariaceae, Stschapoviaceae, Tilopteridaceae, Heterochordariaceae, Bacillariophyceae, Aminariaceae, Phaeophyceae, Raphidiophyceae, Eumastigophyceae, Xanthophyceae, Ishigeaceae, Florideophyceae, Scytothamnaceae or their derivatives, species and mixtures thereof. However, those skilled in the art will appreciate that it is possible to utilize any other algae known in the art from other family, without departing from the scope of the invention.

According to still further embodiment, the algae is at least one belonging to the genus selected from, but not limited to *Spirulina* Sp., *Nitzschia* Sp., *Navicula* Sp., *Ahnfeltia* Sp., *Anikstrodesmis* Sp., *Arthrospira* Sp., *Anabaena* Sp., *Psedoanabeana* Sp., *Nannochloris* Sp. *Asteromenia* Sp., *Botryocladia* Sp., *Chlorella* Sp., *Haematococcus* Sp., *Dunaliella* Sp., *Selenasirum* Sp., *Nannochhropsis* Sp., *Scenedesm* Sp., *Graciaria* Sp., *Oscillatoria* Sp., *Phormidium* Sp., *Nemastoma* Sp., *Amphora* Sp., *Oehromonas* Sp. *Cyanidioschyzon* Sp., *Caulerpa* Sp., *Dictyosphaeria* Sp., *Haliptilon* Sp., *Atractophora* Sp., *Valonia* Sp., *Boodlea* Sp., *Gymnopilus* sp., *Melanothamnus* sp., *Turbeneria* sp., *Mastigocladopsis* sp., *Gelidiella* Sp., *Ceratodictyon* Sp., *Pneophyllum* Sp., *Kallymenia* Sp., *Predaea* Sp, *Siphonocladus* Sp., *Cladophoropsis* Sp., *Amphiplexia* Sp., *Lemanea* Sp., *Mesophyllum* Sp., *Palmaria* Sp., *Cladosiphon* Sp., *Schmitzia* Sp., *Colpomenia* Sp., *Cryptophycées* Sp., *Metagoniolithon* Sp., *Hydrolithon* Sp., *Hypoglossum* Sp., *Seirospora* Sp., *Jania* Sp., *Metamastophora* Sp., *Amphiroa* Sp., *Acanthophora* Sp., *Chondrus* Sp., *Cottoniella* Sp., *Pleonosporium* Sp., *Ditria* Sp., *Endosiphonia* Sp., *Doxodasya* Sp., *Drewiana* Sp., *Dictyomenia* Sp., *Antithamnion* Sp., *Platysiphonia* Sp., *Heterodoxia* Sp., *Dasyclonium* Sp., *Chondria* Sp., *Haraldiophyl-*

*lum* Sp., *Aglaothamnion* Sp., *Struvea* Sp., *Sarcomenia* Sp., *Acrothamnion* Sp., *Martensia* Sp., *Lejolisia* Sp., *Haloplegma* Sp., *Griffithsia* Sp., *Glaphrymenia* Sp, *Dasya* Sp., *Acrosorium* Sp., *Spyridia* Sp., *Hemineura* Sp., *Wrangelia* Sp., *Trithamnion* Sp., *Dasyphila* Sp., *Claudea* Sp., *Corallophila* Sp., *Perischelia* Sp., *Monosporus* Sp., *Carpothamnion* Sp., *Guiryella* Sp., *Gattya* Sp., *Mastocarpus* Sp., *Anotrichium* Sp., *Centroceras* Sp., *Ceramium* Sp., *Caulerpa* Sp., *Vanvoorstia* Sp., *Euptilocladia* Sp., *Titanophora* Sp., *Tanakaella* Sp., *Asparagopsis* Sp., *Lithophyllum* Sp., *Acrochaetium* Sp., *Euptilota* Sp., *Audouinella* Sp., *Botryococcus* Sp., *Actmanthes* Sp., *Ahnfeltiopsis* Sp., *Agmenemum* Sp., *Cochlodinium* Sp., *Amphiprora* Sp., *Anftistrodesmus* Sp., *Ammsirodesnms* Sp., *Borodinetta* Sp., *Carteria* Sp., *Stylonema* Sp., *Chaetoceros* Sp., *Chlamydomas* Sp., *Chlorococcuni* Sp., *Chlorogoni* Sp., *Chroomonas* Sp., *Chrysosphaera* Sp., *Ciicosphaera* Sp., *Crypthecodinium* Sp., *Cryptomonas* Sp., *Cyclotella* Sp., *Dimaliella* Sp., *Eremosphaera* Sp., *Ellipsoidon* Sp., *Euglena* Sp., *Franceia* Sp., *Gloeocapsa* Sp., *Fragilaria* Sp., *Gleocapsa* Sp., *Gloeothamnion* Sp., *Cyanospira* Sp., *Hymenomonas* Sp., *Bockrysis* Sp., *Hochrysis* Sp., *Lepocinclis* Sp., *Stauroneis* Sp., *Micraclinium* Sp., *Chrysymenia* Sp., *Micractinhnn* Sp., *Monaraphidium* Sp., *Nannochloris* Sp., *Navicida* Sp., *Porphyridium* Sp., *Nizymania* Sp., *Scenedesmus* Sp., *Synechoccus* Sp. *Navicul* Sp., *Nephrochloris* Sp., *Odontella* Sp., *Muriellopsis* Sp., *Tschia* Sp., *Nitzschia* Sp., *Isochrysis* Sp., *Phaedactylum* Sp., *Lyngbya* Sp., *Aphanizomenonflos* Sp., *Ochromonas* Sp., *Oocyst* Sp., *Pamchlorelta* Sp., *Peyssonnelia* Sp., *Pascheria* Sp., *Pavlova* Sp., *Phaeodactyhan* Sp., *Cylindrospermum* Sp., *Tolypothrix* Sp., *Hapalosiphon* Sp., *Cylindrotheca* Sp., *Anacystis* Sp., *Ertilissima* Sp., *Aulosira* Sp., *Phortmdium Sp., Platytnonas* Sp., *Pleurochrysis* Sp., *Leptolyngbya* Sp., *Neochloris* Sp., *Prototheca* Sp., *Pseudochlorella* Sp., *Hormotilopsis* Sp., *Gyrodinium* Sp., *Ellipsoidion* Sp., *Pyramimonas* Sp., *Pyrobotrys* Sp., *Sarcinoid* Sp., *Schizochytrmm* Sp., *Spirogyra* Sp., *Stichococcus* Sp., *Synechococcas* Sp., *Synechocystisf* Sp., *Tagetes* Sp., *Tetraedron* Sp., *Tetraselmis* Sp., *Thalassiosira* Sp., *Viridiella* Sp., *Alaria* Sp., *Saccharina* Sp., *Coelarthrum* Sp., *Nereocystis* Sp., *Laminaria* Sp., *Porphyra* Sp., *Phaeocystis* Sp., *Aphanocapsa* Sp., *Phacelocarpus* Sp., *Ulva* Sp., *Himanthalia* Sp., *Cyanothece* Sp., *Ascophyllum* Sp., *Focus* Sp., *Kappaphycus* Sp., *Betaphycus* Sp., *Gelidium* Sp., *Planktothricoides* Sp., *Prochlorococcus* Sp., *Prochloron* Sp., *Prochlorothrix* Sp., *Blastophysa* Sp., *Pedinomonas* Sp., *Resultor* Sp., *Marsupiomonas* Sp., *Chlorokybus* Sp., *Coleochaete* Sp., *Awadhiella* Sp., *Prymnesiophycees* Sp., *Radioramus* Sp., *Conochaete* Sp., *Lithothamnion* Sp., *Phymatolithion* Sp., *Portieria* Sp., *Eustigmatophyte* Sp., *Amphidinum* Sp., *Micractinium* Sp., *Sargassum* Sp., *Curdiea* Sp., *Coelothrix* Sp., *Fucus* Sp., *Eklonia* Sp., *Chlamydomonas* Sp., *Cladophora* Sp., *Gelidiopsis* Sp., *Agmenellum* Sp., *Desmodesmus* Sp., *Halydris* Sp., *Chlorococcum* Sp., *Glossomastix* Sp., *Iridaea* Sp., *Acrosiphonia* Sp., *Goniochloris* Sp., *Gloeothece* Sp., *Emiliana* Sp., *Codium* Sp., *Monochrysis* Sp., *Palma* Sp., *Acetabularia* Sp., *Phaffia* Sp., *Platymonia* Sp., *Mphora* Sp., *Rhodymenia* Sp., *Analipus* Sp., *Egregia* Sp., *Chaetomorph* Sp., *Gymnogongrus* Sp., *Asperococcus* Sp., *Bryopsis* Sp., *Rhizoclonium* Sp., *Gloiocladia* Sp., *Ecklonia* Sp, *Girgatina* Sp., *Hymenocladia* Sp., *Lomentaria* Sp., *Schizochytrium* Sp., *Aphanotece* Sp., *Plocamium* Sp., *Constantinea* Sp., *Cryptosiphonia* Sp., *Webervanboassea* Sp., *Lessoniopsis* Sp., *Chondracanthus* Sp., *Dictyopteris* Sp., *Farlowia* Sp., *Anadyomene* Sp., *Apelvetia* Sp., *Endocladia* Sp., *Coralline* Sp., *Thraustochytrium* Sp., *Osmundea* Sp., *Callophyllis* Sp.M *Calliarthron* Sp., *Monoraphidium* Sp., *Penicillus* Sp., *Meristotheca* Sp., *Wrack* Sp., *Cosmocladium* Sp., *Calothrix* Sp., *Polysiphonia* Sp., *Prionitis* Sp., *Leathesia* Sp., *Polyneura* Sp., *Pelvetiopsis* Sp., *Chlamidonomas* Sp., *Neorhodomela* Sp., *Microdictyon* Sp., *Melobesia* Sp., *Dinoflagellate* Sp., *Delesseria* Sp., *Postelsia* Sp., *Microcladia* Sp., *Dilsea* Sp., *Halimeda* Sp., *Chroococus* Sp., *Phaeodactylum* Sp., *Semnocarpoa* Sp., *Champia* Sp., *Erythrophyllum* Sp., *Chodium* Sp., *Paonia* Sp., *Ulothrix* Sp., *Gracilaria* Sp., *Rivularia* Sp., *Phromidium* Sp., *Stypopodium* Sp., *Erythrocladia* Sp., *Bracchiomonas* Sp., *Coradophylum* Sp., *Cyanophyta* Sp., *Dysmorphococcus* Sp., *Cystoseira* Sp., *Dilophus* Sp., *Gloiotrichus* Sp., *Liagora* Sp., *Eisenia* Sp., *Ganonema* Sp., *Hennedya* Sp., *Codiophyllum* Sp., *Ecklonia* Sp., *Distromium* Sp., *Sparlingia* Sp., *Gastrocelonium* Sp., *Claviclonium* Sp., *Pelvetia* Sp., *Mazzaella* Sp., *Lobophora* Sp., *Pterocladia* Sp., *Scinaia* Sp., *Galaxaura* Sp., *Gloiopeltis* Sp., *Scillatoria* Sp., *Hypnea* Sp., *Hormophysa* Sp., *Dotyophycus* Sp., *Opuntiella* Sp., *Nannochloropsis* Sp., *Myriodesma* Sp., *Tricleocarpa* Sp., *Trichogloea* Sp., *Yamadaella* Sp., *Sebdenia* Sp., *Gelinaria* Sp., *Prymnesium* Sp., *Herposiphonia* Sp., *Jeannerettia* Sp., *Kuetzingia* Sp., *Laurencia* Sp., *Lenormandiopsis* Sp., *Halymenia* Sp., *Eucheuma* Sp., *Erythroclonium* Sp., *Achnanthes* Sp., *Rhodopeltis* Sp., *Dudresnaya* Sp., *Halosaccion* Sp., *Zonaria* Sp., *Areschougia* Sp., *Hincksia* Sp., *Osmundaria* Sp., *Placophora* Sp., *Lophocladia* Sp., *Macrocystis* Sp., *Callophycus* Sp., *Microcoleus* Sp., *Epiphloea* Sp., *Acrosymphyton* Sp., *Cryptonemia* Sp., *Enteromorpha* Sp., *Neurymenia* Sp., *Lophosiphonia* Sp., *Microcystis* Sp., *Protokuetzingia* Sp., *Leveillea* Sp., *Caulocystis* Sp., *Hydroclathrus* Sp., *Scaberia* Sp., *Rosenvingea* Sp., *Schizothrix* Sp., *Rhodella* Sp., *Spirocladia* Sp., *Acrochaetium Robustum Brgesen, Tolypiocladia* Sp., *Tylotus* Sp., *Dicranema* Sp., *Pachydictyon* Sp., *Austronereia* Sp., *Sporochnus* Sp., *Craspedocarpus* Sp., *Solieria* Sp., *Encyothalia* Sp., *Nanococcus* Sp., *Gracilaria* Sp., *Grateloupia* Sp., *Hildenbrandia* sp., *Amphiroa* Sp., *Cheilosporum* Sp., *Corallina* Sp., *Hydrolithon* sp., *Hydrolithon* sp., *Jania* Sp., *Lithophyllum* sp., *Catenella* Sp., *Chondracanthus* Sp., *Hypnea Flagelliformis* sp., *Ahnfeltiopsis* Sp., *Champia* Sp., *Gastroclonium* Sp., *Gelidiopsis* Sp., *Gayliellaflaccida* sp., *Aglaothamnion* Sp., *Crouania* Sp., *Ptilothamnion* Sp., *Dasya* Sp., *Caloglossa* Sp., *Aloglossa* Sp., *Erythroglossum* Sp., *Martensia Fragilis* sp., *Bostrychia* Sp., *Chondria* Sp., *Herposiphonia* Sp., *Laurencia Obtuse* sp., *Neosiphonia* Sp., *Polysiphonia* Sp., *Vaucheria* Sp., *Feldmannia* sp., *Hinksia* Sp., *Ralfsia* sp., *Sphacelaria* Sp., *Canistrocarpus* Sp., *Dictyota* Sp., *Padina* Sp., *Pyropia* Sp., *Spatoglossum* Sp., *Spatoglossum* Sp., *Stoechospermum* Sp., *Chnoospora* Sp., *Iyengaria* Sp., *Gayralia* Sp., *Chaetomorpha* Sp., *Cladophora* Sp., *Cladophoroposis* Sp., *Phyllodictyon* Sp., *Valoniopsis* Sp., *Bryopis* Sp., *Caulerpa* Sp., *Avrainvillea* Sp., *Chlorodesmis* Sp., *Petrocelis* Sp., *Ectocarpus* Sp., *Bossiella* Sp., *Candida* Sp., or derivatives and mixtures thereof. However, those skilled in the art will appreciate that it is possible to utilize any other genus of algae known in the art, without departing from the scope of the invention. The algae are commercially manufactured and available through various companies.

According to another embodiment, the algae is at least one species selected from, but not limited to: *Anabena cylindrica, Bryopsis australis, Bryopsis minor, Botryococcus Braunii, Actmanthes Orientalis, Amphiprora Hyaline, Amphora Coffeiformis, Amphora Cqffeifoiinis* Var. *Linea, Chlorideila Simplex, Apelvetia Canaliculata, Caulerpa Taxifolia, Amphora Cqffeiformis* Var. *Punctata, Amphora Cqffeiformis* Var. *Taylori, Laurencia Spectabilis, Gymnogongrus Crenulatus, Opuntiella Californica, Gymnogon-*

*grus Griffithsiae, Achnanthes Orientalis, Cladosiphon Filum, Goniochloris Sculpta, Ecklonia Cava, Osmundea Spectabilis, Neorhodomela Larix, Asperococcus Bullosus, Caulerpa Cactoides, Gelidium Micropterum, Caulerpa Cliftonii, Caulerpa Cupressoides, Caulerpa Fergusonii, Caulerpa Lentillifera, Caulerpa Mexicana, Ahnfeltia Plicata, Caulerpa Obscura, Caulerpa Racemosa, Caulerpa Racemosa* Var. *Corynephora, Caulerpa Racemosa* Var. *Laetivirens, Caulerpa Racemosa* Var. *Lamourouxii, Caulerpa Racemosa* Var. *Peltata, Caulerpa Serrulata, Caulerpa Simpliciuscula, Asteromenia Peltata, Botryocladia Skottsbergii, Botryocladia cabillaceae, Ceratodictyon Spongiosum, Chrysymenia Kaernbachii, Chrysymenia Ornata, Coelarthrum Cliftonii, Coelothrix Irregularis, Chara globularis, Gelidiopsis Variabilis, Gymnopilus edulis, Tetraselmis maculate, Prymnesium parvum, Chlamydomonas rheinhardii, Euglena gracilis, Caulerpa scalpelliformis, Padina pavonica, Sargassum tenerrimum, Sargassum wightii, Chondria armata, Caulerpa racemosa, Lyngby majuscule, Prasiola crispa, Gloiocladia Halymenioides, Pterocladia Capillacea, Prymnesium Parvum, Gloiocladia Indica, Gloiocladia Rubrispora, Gloiosaccion Brownii, Gelidium Pusillum, Hymenocladia Usnea, Phymatolithion Calcereum, Lithothamnion Calcareoum, Herposiphonia Secunda, Herposiphonia Secunda F. Tenella, Heterostroma Nereidiis, Jeannerettia Lobata, Jeannerettia Pedicellata, Kuetzingia Canaliculata, Laurencia Brongniartia, Laurencia Cruciata, Laurencia Filiformis, Laurencia Majuscula, Laurencia Papillosa, Lenormandiopsis Latifolia, Leveillea Jungermannioides, Lophocladia Harveyi, Lophosiphonia Prostrata, Neurymenia Fraxinifolia, Osmundaria Spiralis, Placophora Binderi, Polysiphonia Decipiens, Polysiphonia Gracilis, Protokuetzingia Australasica, Spirocladia Barodensis, Tolypiocladia Glomerulata, Amphiroa Anceps, Amphiroa Foliacea, Amphiroa Gracilis, Haliptilon Roseum, Hydrolithon Farinosum, Hydrolithon Onkodes, Jania Pulchella, Lithophyllum Bermudense, Mesophyllum Engelhartii, Mesophyllum Erubescens, Mesophyllum Funafutiense, Metagoniolithon Radiatum, Metagoniolithon Stelliferum, Metamastophora Flabellata, Pneophyllum Fragile, Gelidium Austral, Pterocladia Lucida, Gelidiella Pannosa, Amphiplexia Hymenocladioides, Claviclonium Ovatum, Hennedya Crispa, Areschougia Ligulata, Callophycus Serratus, Callophycus Oppositifolius, Erythroclonium Sonderi, Eucheuma Denticulatum, Eucheuma Gelatinum, Eucheuma Speciosum, Meristotheca Papulosa, Solieria Robusta, Craspedocarpus Venosus, Dicranema Revolutum, Tylotus Obtusatus, Acrosymphyton Taylorii, Dudresnaya Capricornica, Rhodopeltis Borealis, Hypnea Spinella, Hypnea Valentiae, Stylonema Alsidii, Audouinella Saviana, Asparagopsis Armata, Asparagopsis Taxiformis, Acrothamnion Preissii, Aglaothamnion Cordatum, Anotrichium Tenue, Antithamnion Antillanum, Antithamnion Armatum, Antithamnion Hanovioides, Carpothamnion Gunnianum, Centroceras Clavulatum, Ceramium Filicula, Ceramium Flaccidum, Ceramium Isogonum, Ceramium Macilentum, Ceramium Mazatlanense, Ceramium Puberulum, Ceramium Sherpherdii, Ceramium Sympodiale, Corallophila Huysmansii, Dasyphila Preissii, Drewiana Nitella, Euptilocladia Spongiosa, Euptilota Articulata, Gattya Pinnella, Griffithsia Ovalis, Guiryella Repens, Haloplegma Preissii, Lejolisia Aegagropila, Monosporus Indicus, Peri schelia Glomulifera, Pleonosporium Caribaeum, Seirospora Orientalis, Spyridia Filamentosa, Tanakaella Itonoi, Trithamnion Gracilissimum, Wrangelia Plumosa, Dasya Iyengarii, Dasya Pilosa, Acrosorium Decumbens, Claudea Elegans, Cottoniella Filamentosa, Haraldiophyllum Erosum, Hemineura*

*Frondosa, Heterodoxia Denticulata, Hypoglossum Caloglossoides, Hypoglossum Revolutum, Martensia Australis, Martensia Fragilis, Platysiphonia Corymbosa, Platysiphonia Delicata, Platysiphonia Marginalis, Sarcomenia Delesserioides, Acanthophora Dendroides, Acanthophora Spicifera, Chondria Curdieana, Chondria Dangeardii, Chondria Lanceolata, Dasyclonium Flaccidum, Dasyclonium Incisum, Dictyomenia Sonderi, Dictyomenia Tridens, Ditria Expleta, Doxodasya Bolbochaete, Endosiphonia Spinuligera, Rhodymenia Leptophylla, Rhodymenia Sonderi, Webervanboassea Splachnoides, Glaphrymenia Pustulosa, Kallymenia Cribrogloea, Kallymenia Cribrosa, Nemastoma Damaecornis, Predaea Laciniosa, Predaea Weldii, Titanophora Weberae, Nizymania Conferta, Peyssonnelia Capensis, Peyssonnelia Inamoena, Phacelocarpus Alatus, Portieria Hornemannii, Curdiea Obesa, Gracilaria Canaliculata, Gracilaria Preissiana, Gracilaria Textorii, Codiophyllum Flab elliforme, Erythrocladia Irregularis, Cryptonemia Kallymenioides, Epiphloea Bullosa, Gelinaria Ulvoidea, Halymenia Floresia, Sebdenia Flabellata, Porphyra Crispate Kjellman, Gracilaria Corticata, Gracilaria Foliifera, Gracilaria Verrucosa, Grateloupia Filicina, Grateloupia Filicina F. Horrida, Grateloupia Lithophila, Peyssonnelia Obscura, Hildenbrandia Rubra, Amphiroa Anceps, Amphiroa Fragilissima, Amphiroa Rigida, Cheilosporum Spectabile, Corallina Officinalis, Hydrolithon Farinosum, Hydrolithon Reinboldii, Jania Rubens, Lithophyllum Orbiculatum, Catenella Caespitose, Chondracanthus Acicularis, Hypnea Flagelliformis, Hypnea Musciformis, Hypnea Spinella, Hypnea Valentiae, Ahnfeltiopsis Pygmaea, Champia Compressa, Champia Parvula, Gastroclonium Compressum, Gelidiopsis Variabilis, Antithamnion Cruciatum, Ceramium Cimbricum, Ceramium Cruciatum, Aglaothamnion Tenuissimum, Crouania Attenuata, Ptilothamnion Speluncarum, Wrangelia Argus, Dasya Ocellata, Caloglossa Leprieurii, Aloglossa Ogasawaraensis, Erythroglossum Lusitanicum, Hypoglossum Hypoglossoides, Acanthophora Muscoides, Bostrychia Radicans, Bostrychia Tenella, Chondria Armata, Chondria Capillaries, Herposiphonia Secunda, Laurencia Obtuse, Neosiphonia Ferulacea, Polysiphonia Atlantica, Polysiphonia Denudate, Vaucheria Longicaulis, Feldmannia Indica, Feldmannia Irregularis, Hinksia Mitchelliae, Ralfsia Verrucosa, Sphacelaria Rigidula, Canistrocarpus Cervicornis, Canistrocarpus Crispatus, Canistrocarpus Magneanus, Dictyopteris Australis, Dictyota Bartayresiana, Dictyota Ceylanica, Dictyota Ciliolate, Dictyota Dichotoma, Dictyota Divaricata, Dictyota Dumosa, Padina Antillarum, Padina Australis, Padina Boryana, Padina Gymnospora, Padina Pavonica, Spatoglossum Asperum, Spatoglossum Variabile, Stoechospermum Polypodioides, Chnoospora Minima, Colpomenia Sinuosa, Iyengaria Stellata, Rosenvingea Orientalis, Sargassum Cinctum, Sargassum Cinereum, Sargassum Crassifolium, Sargassum Glaucescens, Sargassum Ilicifolium, Sargassum Plagiophyllum, Sargassum Polycystum, Sargassum Prismaticum, Sargassum Swartzii, Sargassum Tenerrimum, Sargassum Vulgare, Gayralia Oxysperma, Ulva Clathrata, Ulva Compressa, Ulva Conglobata, Ulva Flexuosa, Ulva Intestinalis, Ulva Rigida, Ulva Taeniata, Chaetomorpha Antennina, Chaetomorpha Linum, Chaetomorpha Spiralis, Cladophora Bombayensis, Cladophora Coelothrix, Cladophora Glomerata, Cladophora Lehmanniana, Cladophora Prehendens, Cladophora Prolifera, Cladophora rhizoclonioidea, Cladophora Saracenica, Cladophora Socialis, Cladophora Vagabunda, Rhizoclonium Tortuosum, Boodlea Composite, Cladophoroposis Sundanensis, Phyllodictyon Anastomosans, Valoniopsis*

Pachynema, Bryopis Hypnoides, Bryopsis Pennata, Bryopsis Plumose, Caulerpa Peltata, Caulerpa Racemosa, Caulerpa Scalpelliformis, Caulerpa Sertularioides, Caulerpa Verticillata, Avrainvillea Erecta, Chlorodesmis Hildebrandtii, Dotyophycus Abbottiae, Ganonema Farinosa, Gloiotrichus Fractalis, Liagora Setchellii, Trichogloea Requienii, Galaxaura Marginata, Galaxaura Obtusata, Galaxaura Rugosa, Scinaia Tsinglanensis, Tricleocarpa Cylindrica, Plocamium Preissianum, Champia Compressa, Champia Pravula, Champia Zostericola, Lomentaria Corallicola, Lomentaria Monochlamydea, Semnocarpoa Minuta, Caulerpa Webbiana, Caulerpa Racemosa Var. Turbinata, Neorhodomela Oregona, Odonthalia Floccose, Odonthalia Floccosa, Forma Comosa, Odonthalia Washingtoniensis, Ecklonia Kurome, Mastocarpus Jardinii, Acetabularia Calyculus, Halimeda Cuneata, Porphyra Suborbiculata, Porphyra Vietnamensis, Cladophoropsis Herpestica, Siphonocladus Tropicus, Struvea Plumosa, Rhodella Maculate, Polysiphonia Hendryi, Ecklonia Stoloifera, Microcladia Borealis, Microdictyon Umbilicatum, Ecklonia Maxima, Ecklonia Radiate, Nereocystis Luetkeana, Penicillus Nodulosus, Ecklonia Bicyclis, Ecklonia Arborea, Eisenia Bicyclis, Eisenia Arboraea, Halosaccion Glandiforme, Amphora Coffeiformis Var. Tenuis, Dictyosphaeria Cavernosa, Dictyopteris Muelleri, Dictyopteris Plagiogramma, Dictyota Ciliolata, Dictyota Dichotoma, Dictyota Dichotoma Var Intricata, Dictyota Furcellata, Dictyota Mertensii, Dictyota Naevosa, Dilophus Crinitus, Dilophus Fastigiatus, Dilophus Robustus, Distromium Flabellatum, Lobophora Variegata, Pachydictyon Paniculatum, Sargassum Boryi, Sargassum Decurrens, Sargassum Distichum, Sargassum Fallax, Sargassum Ligulatum, Sargassum Linearifolium, Sargassum Podacanthum, Sargassum Spinuligerum, Sargassum Tristichum, Padina Boergesenii, Padina Elegans, Padina Sanctae-Crucis, Padina Tenuis, Stypopodium Australasicum, Stypopodium Flabelliforme, Zonaria Turneriana, Hincksia Mitchelliae, Caulocystis Uvifera, Cystoseira Trinodis, Hormophysa Cuneiformis, Myriodesma Quercifolium, Scaberia Agardhii, Ecklonia Radiata, Hydroclathrus Clathratus, Sphacelaria Biradiata, Sphacelaria Novae-Hollandiae, Sphacelaria Rigidula, Austronereia Australis, Encyothalia Cliftonii, Sporochnus Comosus, Dictyosphaeria Versluysii, Amphora Delicatissima, Amphora Delicatissima Var. Capitata, Cosmocladium Perissum, Anadyomene Brownie, Ammsirodesnms Falcatus, Dilsea Californica, Gigartina Agardhii, Delesseria Decipiens, Polyneura Latissima, Mastocarpus Papillatus, Cryptosiphonia Woodii, Porphyra Pseudolanceolata, Melobesia Mediocris, Boekelovia Hooglandii, Codium Duthieae, Codium Geppiorum, Codium Laminarioides, Codium Lucasii, Codium Spongiosum, Plocamium Cartilagineum, Farlowia Mollis, Hypnea Musciformis, Meristotheca Senegalensis, Sparlingia Pertussa, Meristotheca Papulosa, Halydris Siliquosa, Rhodymenia Pertussa, Botryococcus Brmmii, Botryococcus Sudeticus, Erythrophyllum Delesserioides, Gigartina Papillata, Bracteococcus Minor, Egregia Menziesii, Laminaria Sinclairii, Bracteococcus Medionucleats, Lessoniopsis Littoralis, Chaetoceros Gracilis, Valonia Macrophysa, Gloiopeltis Furcata, Constantinea Simplex, Colpomenia Bullosa, Ahnfeltiopsis Linearis, Colpomenia Peregrine, Endocladia Muricata, Callithamnion Pikeanum, Choetoceros Muejleri, Calliarthron Tuberculosum, Choetoceros Mueeri Var. Subsalsum, Chlamydomas Perigratmlata, Chlorella Anitrata, Chlorella Antarctica, Chloreuaureo viridis, Chlamydomonas Rheinhardii, Neochloris Oleoabundans, Emiliana Huxleyi, Chlamydomonas Sajao, Gigartina Exasperate, Chondracanthus Exasperates, Chlamydomonas Moewusii, Nanococcus Vulgaris, Pelvetiopsis Limitata, Chlorella Ellipsoidea, Postelsia Palmaeformis, Chlorelia Etmrsonii, Sargassum Muticum, Chlorell Fusco, Eklonia Maxima, Chlorella Fusca Var. Vacuolate, Ceramium Rubrum, Chlorella Glucolropha, Leathesia Marina, Chlorella Infiisionum, Analipus Japonicas, Chlorella Infimon M Var. Actophija, Desmodesmus Asymmetricus, Chlorella Infustomtm Var. Attxenophila, Chlorella Kessleri, Chlorella Lobaphord, Chlorella Luieoviridis, Chlorella Luieoviridis Var. Aureovmdts, Ralfsia Fungiformis, Ceramium Codicola, Chlorella Hiteavmdis Var, Hitescens, Chlorella Riniata, Chlorella Minttssima, Chlorella Mutabilis, Chlorella Nocturna, Chlorella Ovalis, Costaria Costata, Desmarestia Ligulata, Fucus Vesiculosus, Fucus Serratus, Fucus gardneri, Chlorella Parva, Chlorella Pyrenoidosa, Chlorella Phoiophila, Chlorella Pringsheimii, Chlorella Protothecoides, Chlorella Protat Ecoides Var. Acidicola, Chlorella Regularis, Prionitis Sternbergii, Chlorella Regularis Var. Minima, Chlorella Regularis Var. Umbricata, Chlorella Reisiglii, Chlorella Saecharophila, Chlorella Saecharophila Var. Ellipsoidea, Chlorella Salina, Chlorella Simplex, Chlorell Sorokmiana, Chlorella Sphaerica, Chlorella Stigmatophora, Chlorella Var. Iellii, Chlorella Vulgaris, Codium Setchellii, Corallina Vancouveriensis, Chlorella Vulgaris Fo. Tertia, Chlorella Vulgaris Var. Autotroph Ica, Chlorella Vulgaris Var. Viridis, Chlorella Vulgaris Var. Vulgaris, Chlorella Vulgaris Var Vulgaris Fo. Tertia, Chlorella Vulgaris Var. Vulgaris Fo. Viridis, Chlorella Xamhella, Chlorella Zofingiensis, Chlorella Ireboux-ioides, Chlorococcum Infusiovum, Chlorogoni N, Crypthecodinium Cohnii, Cyclotella Cryptica, Cyclotejla Meneghiniana, Dimaliella Hardawil, Dunaliella Bioculata, Dimaliella Granulate, Dunaliella Maritime, Dunaliella Minuta, Dimaliella Parva, Dunaliella Peircei, Dunaliella Primolecta, Bossiella Plumose, Dunaliella Salina, Dimaliella Terricoia, Dunaliella Tertiolecta, Dunaliella Viridis, Dunaliella Tertioiecta, Eremosphaera Viridis, Euglena Gracilis, Fragilari Crotonensis, Haematococcus Pluvialis, Hochrysis Galbana, Monaraphidium falcatus, Nannochloropsis Salina, Navicida Accepiata, Navicula Biskanterae, Navicula Pseudotenelloides, Porphyridium Cruentum, Porphyridium Parvum, Scenedesmus Dimorphus, Navicul Pellicidosa, Navicida Saprophtla, Odontella Aurita, Tschia Communis, Nitzschia Alexandrine, Nitzschia Clostenum, Nitzschia Communis, Nitzschia D Sipata, Nitzschia Frustuhmi, Nitzschia Hantzschiana, Nitzschia Inconspicua, Nitzschia Intermedia, Cladophora Columbiana, Nitzschia Microcephala, Nitzschia Pusilla, Isochrysis Galbana, Phaedactylum, Lyngbya Majuscule, Aphanizomenonflos, Nitzschia Pusilla E Iptica, Nitzschia Pusilla Monoensis, Palmaria Mollis, Rhodymenia Palmata Fistulinella Mollis, Nitzschia Quadrangular, Oocystis Pusilla, Oscillatoria Li. Nme. Tica, Acrosiphonia Coalita, Oscillatoria Subbrevis, Pamchlorelta Kessleri, Pascheria Acidophila, Phaeodactyhan Tricomutwn, Tolypothrix Tenuis, Hapalosiphon Fontinalis, Pleurochrysis Camerae, Pleurochrysis Dentate, Pleurochrysis Carterae, Prototheca Wickerhamii, Prototheca Stagnora, Prototheca Ponoricensis, Prototheca Moriformis, Prototheca Zopfii, Pseudochlorella Aquatica, Rhodococcus Opaciis, Sarcinoid Chrysophyte, Scenedesmus Annatus, Scenedesmus Obliquus, Scenedesmus Quadricauda, Schizochytrmm, Spirulina Platensis, Spirulina Maxima, Synechocystisf, Tagetes Erecta, Tetrasehnis Suecica, Codium Fragile, Thalassiosira Weissflogii, Viridiella Fridericiana, Palmaria Palmate, Alaria Esculenta, Saccharina Latissima, Saccharina Sessilis, Saccharina Dentigera, Laminaria Saccharina, Porphyra Umbilicalis, Alaria

*Marginata, Ulva Lactuca, Ulva Armoricana, Laminaria Digitata, Himanthalia Elongata, Ascophyllum Nodosum, Laminaria Longicruris, Scytosiphon Dotyi, Scytosiphon Lomentaria, Porphyra Yezoensis, Focus Vesiculosus, Kappaphycus Alvarezii, Betaphycus Gracilaria, Gelidium Pterocladia, Soranthera Ulvoidea, Chondrus Crispus, Mastocarpus Stellatus, Gracilaria Edulis, Phaeostrophion Irregulare, Enteromorpha Intestinalis, Enteromorpha Compressa, Enteromorpha flexuso, Pyropia yezoensis, Macrocystis Pyrifera, Asparagopsis Armata, Mazzaella Flaccida, Iridaea Flaccid, Mazzaella Oregona, Iridaea Oregona, Iridaea Heterocarpa, Mazzaella Parksii, Iridaea Cornucopiae, Mazzaella Splendens, Iridaea Cordataor* mixtures thereof. However, those skilled in the art will appreciate that it is possible to utilize any other species known in the art, without departing from the scope of the invention. The algaes are commercially manufactured and available through various companies.

According to yet another embodiment, algae is any one of *Spirulina, Arthrospira, Chlorella, Anabaena, Sargassum, Scenedesmus, Aphanizomenon, Dunaliella, Phymatolithion, Lithothamnium, Ascophyllum, Enteromorpha, Tetraselmis, Prymnesium, Chlamydomonas, Euglena, Caulerpa, Padina, Urophora, Chondria, Caulerpa, Lyngby, Prasiola, Gymnopilus, Melanothamnus, Turbeneria, Mastigocladopsis, Hydroclathrus, Padina, Cystoseira, Laminaria, Fucus, Ulva* or their species and mixtures thereof. According to further embodiment, algae can be *Spirulina Plantensis, Spirulina Maxima, Anabaena Cylindrica, Aphanizomenon Flos-Aquae, Enteromorpha Intestinalis, Enteromorpha Compressa, Enteromorpha flexuso, Fucus gardneri, Scenedesmus Obliquus, Ascophyllum Nodosum, Phymatolithion calcereum, Lithothamnium calcereum, Aphanizomenon Flos-Aquae, Dunaliella Salina, Tetraselmis maculate, Prymnesium parvum, Chlamydomonas rheinhardii, Euglena gracilis, Caulerpa scalpelliformis, Padina pavonica, Sargassum tenerrimum, Urophora fasciata, Urophora lactuca, Sargassum wightii, Chondria armata, Caulerpa racemosa, Lyngby majuscule, Prasiola crispa, Gymnopilus edulis* or their species and mixtures thereof. However, those skilled in the art will appreciate that it is possible to utilize any other species of *Spirulina, Arthrospira, Anabaena, Scenedesmus, Sargassum, Ascophyllum, Aphanizomenon, Dunaliella, Phymatolithion, Lithothamnium, Tetraselmis, Prymnesium, Chlamydomonas, Euglena, Caulerpa, Padina, Urophora, Chondria, Caulerpa, Lyngby, Prasiola, Gymnopilus, Enteromorpha, Fucus* or different algaes known in the art, without departing from the scope of the invention. The algaes are commercially cultivated, manufactured and available through various companies.

According to an embodiment, the algae comprises at least 0.1% by weight of the total composition. According to an embodiment, the algae comprises at least 1% by weight of the total composition. According to another embodiment, the algae comprises at least 5% by weight of the total composition. According to another embodiment, the algae comprises at least 10% by weight of the total composition. According to further embodiment, the algae comprises at least 20% by weight of the total composition. According to further embodiment, the algae comprises at least 30% by weight of the total composition. According to further embodiment, the algae comprises at least 40% by weight of the total composition. According to further embodiment, the algae comprises at least 50% by weight of the total composition. According to further embodiment, the algae comprises at least 60% by weight of the total composition. According to further embodiment, the algae comprises at least 70% by weight of the total composition. According to yet another embodiment the algae comprises at least 80% by weight of the total composition. According to another embodiment the algae comprises at least 90% by weight of the total composition.

According to another embodiment the algae comprises at least 95% by weight of the total composition.

According to an embodiment, the agrochemically acceptable excipient comprises surfactants, binders or binding agents, disintegrating agents, fillers or carriers or diluents, spreading agents, coating agents, pigments, colorants, buffers or pH adjusters or neutralizing agents, antifoaming agents or defoamers, penetrants, preservatives, ultraviolet absorbents, UV ray scattering agents, stabilizers, and mixtures thereof. However, those skilled in the art will appreciate that it is possible to utilize additional agrochemically acceptable excipients without departing from the scope of the present invention. The agrochemically acceptable excipients are commercially manufactured and available through various companies.

According to an embodiment, the agrochemical excipients are present in a concentration range of at least 99.9% by weight of the total composition. According to an embodiment, the agrochemical excipients are present in a concentration range of at least 99% by weight of the total composition. According to an embodiment, the agrochemical excipients are present in a concentration range of at least 95% by weight of the total composition. According to an embodiment, the agrochemical excipients are present in a concentration range of at least 90% by weight of the total composition. According to an embodiment, the agrochemical excipients are present in a concentration range of at least 80% by weight of the total composition. According to an embodiment, the agrochemical excipients are present in a concentration range of at least 70% by weight of the total composition. According to an embodiment, the agrochemical excipients are present in a concentration range of at least 60% by weight of the total composition. According to an embodiment, the agrochemical excipients are present in a concentration range of at least 50% by weight of the total composition. According to an embodiment, the agrochemical excipients are present in a concentration range of at least 40% by weight of the total composition. According to an embodiment, the agrochemical excipients are present in a concentration range of at least 30% by weight of the total composition. According to an embodiment, the agrochemical excipients are present in a concentration range of at least 20% by weight of the total composition. According to an embodiment, the agrochemical excipients are present in a concentration range of at least 10% by weight of the total composition.

According to an embodiment, the agrochemical excipients are present in a concentration range of at least 5% by weight of the total composition.

According to an embodiment, the weight ratio of the algae to the agrochemically acceptable excipients is 99:1 to 1:99. According to an embodiment, the weight ratio of algae to the agrochemically acceptable excipients is 90:1 to 1:90. According to an embodiment, the weight ratio of algae to the agrochemically acceptable excipients is 80:1 to 1:80. According to an embodiment, the weight ratio of algae to the agrochemically acceptable excipients is 70:1 to 1:70. According to an embodiment, the weight ratio of algae to the agrochemically acceptable excipients is 60:1 to 1:60. According to an embodiment, the weight ratio of algae to the agrochemically acceptable excipients is 50:1 to 1:50. According to an embodiment, the weight ratio of algae to the agrochemically acceptable excipients is 40:1 to 1:40. According to an embodiment, the weight ratio of algae to the agrochemically acceptable excipients is 30:1 to 1:30. According to an embodiment, the weight ratio of algae to the agrochemically acceptable excipients is 20:1 to 1:20. According to an embodiment, the weight ratio of algae to the agrochemically acceptable excipients is 10:1 to 1:10. According to an embodiment, the weight ratio of algae to the agrochemically acceptable excipients is 5:1 to 1:5. According to an embodiment, the weight ratio of algae to the agrochemically acceptable excipients is 1:1.

According to an embodiment, the agrochemical excipients include at least one of surfactant or binder or disintegrant. According to another embodiment the weight ratio of algae to at least one of surfactant, binder or disintegrant is in the range of 99:1 to 1:50. According to another embodiment the weight ratio of algae to at least one of surfactant, binder or disintegrant is in the range of 99:1 to 1:30. According to another embodiment the weight ratio of algae to at least one of surfactant, binder or disintegrant is in the range of 80:1 to 1:30. According to another embodiment the weight ratio of algae to at least one of surfactant, binder or disintegrant is in the range of 70:1 to 1:30. According to another embodiment the weight ratio of algae to at least one of surfactant, binder or disintegrant is in the range of 60:1 to 1:30. According to another embodiment the weight ratio of algae to at least one of surfactant, binder or disintegrant is in the range of 50:1 to 1:30. According to an embodiment, the weight ratio of algae to at least one of surfactant, binder or disintegrant is 50:1 to 1:20. According to an embodiment, the weight ratio of algae to at least one of surfactant, binder or disintegrant is 50:1 to 1:10. According to an embodiment, the weight ratio of algae to at least one of surfactant, binder or disintegrant is 50:1 to 1:5. According to another embodiment the weight ratio of algae to at least one of surfactant, binder or disintegrant is in the range of 50:1 to 1:1. According to another embodiment the weight ratio of algae to at least one of surfactant, binder or disintegrant is in the range of 40:1 to 1:1. According to another embodiment the weight ratio of algae to at least one of surfactant, binder or disintegrant is in the range of 30:1 to 1:1. According to another embodiment the weight ratio of algae to at least one of surfactant, binder or disintegrant is in the range of 20:1 to 1:1. According to another embodiment the weight ratio of algae to at least one of surfactant, binder or disintegrant is in the range of 18:1 to 1:1. According to another embodiment, the weight ratio of algae to at least one of surfactant, binder or disintegrant is 15:1 to 1:1. According to an embodiment, the weight ratio of algae to at least one of surfactant, binder or disintegrant is 12:1 to 1:1. According to an embodiment, the weight ratio of algae to at least one of surfactant, binder or disintegrant is 10:1 to 1:1. According to another embodiment, the weight ratio of algae to at least one of surfactant, binder or disintegrant is in the range of 9:1 to 1:1. According to an embodiment, the weight ratio of algae to at least one of surfactant, binder or disintegrant is 6:1 to 1:1. According to an embodiment, the weight ratio of algae to at least one of surfactant, binder or disintegrant is 4:1 to 1:1. According to an embodiment, the weight ratio of algae to at least one of surfactant, binder or disintegrant is 1:1. The ratio is dependent on the type of algae, the concentration of the algae, and any other agrochemically active materials being used in the composition.

According to an embodiment the weight ratio of algae to at least one of surfactant, binder or disintegrant is 99:1. According to an embodiment the weight ratio of algae to at least one of surfactant, binder or disintegrant is 90:1. According to an embodiment the weight ratio of algae to at least one of surfactant, binder or disintegrant is 80:1. According to an embodiment the weight ratio of algae to at least one of surfactant, binder or disintegrant is 70:1. According to an embodiment the weight ratio of algae to at least one of surfactant, binder or disintegrant is 60:1. According to an embodiment, the weight ratio of algae to at least one of surfactant, binder or disintegrant is 50:1. According to an embodiment, the weight ratio of algae to at least one of surfactant, binder or disintegrant is 40:1. According to an embodiment, the weight ratio of algae to at least one of surfactant, binder or disintegrant is 30:1. According to an embodiment, the weight ratio of algae to at least one of surfactant, binder or disintegrant is 25:1. According to an embodiment, the weight ratio of algae to at least one of surfactant, binder or disintegrant is 20:1. According to an embodiment, the weight ratio of algae to at least one of surfactant, binder or disintegrant is 18:1. According to an embodiment, the weight ratio of algae to at least one of surfactant, binder or disintegrant is 17:1. According to an embodiment, the weight ratio of algae to at least one of surfactant, binder or disintegrant is 16:1. According to an embodiment, the weight ratio of algae to at least one of surfactant, binder or disintegrant is 15:1. According to an embodiment, the weight ratio of algae to at least one of surfactant, binder or disintegrant is 14:1. According to an embodiment, the weight ratio of algae to at least one of surfactant, binder or disintegrant is 13:1. According to an embodiment, the weight ratio of algae to at least one of surfactant, binder or disintegrant is 12:1. According to an embodiment, the weight ratio of algae to at least one of surfactant, binder or disintegrant is 11:1. According to an embodiment, the weight ratio of algae to at least one of surfactant, binder or disintegrant is 10:1. According to an embodiment, the weight ratio of algae to at least one of surfactant, binder or disintegrant is 9:1. According to an embodiment, the weight ratio of algae to at least one of surfactant, binder or disintegrant is 8:1. According to an embodiment, the weight ratio of algae to at least one of surfactant, binder or disintegrant is 7:1. According to an embodiment, the weight ratio of algae to at least one of surfactant, binder or disintegrant is 6:1. According to an embodiment, the weight ratio of algae to at least one of surfactant, binder or disintegrant is 5:1. According to an embodiment, the weight ratio of algae to at least one of surfactant, binder or disintegrant is 4:1. According to an embodiment, the weight ratio of algae to at least one of surfactant, binder or disintegrant is 3:1. According to an embodiment, the weight ratio of algae to at least one of surfactant, binder or disintegrant is 2:1. According to an embodiment, the weight ratio of algae to at least one of surfactant, binder or disintegrant is 1:1. According to an embodiment, the weight ratio of algae to at least one of surfactant, binder or disintegrant is 1:2. According to an embodiment, the weight ratio of algae to at least one of surfactant, binder or disintegrant is 1:3. According to an embodiment, the weight ratio of algae to at least one of surfactant, binder or disintegrant is 1:4. According to an embodiment, the weight ratio of algae to at least one of surfactant, binder or disintegrant is 1:5. According to an embodiment, the weight ratio of algae to at least one of surfactant, binder or disintegrant is 1:10. According to an embodiment, the weight ratio of algae to at least one of surfactant, binder or disintegrant is 1:20. According to an embodiment, the weight ratio of algae to at least one of surfactant, binder or disintegrant is 1:30.

However, the ratios stated herein are only exemplary and those skilled in the art will appreciate that it is possible to utilize different ratios without departing from the scope of the present invention.

According to an embodiment, the algae is preferably one of *Spirulina* Sp., *Chlorella* Sp., *Ascophyllum* Sp., *Sargassum* Sp., *Lithothamnium* Sp., *Enteromorpha* Sp.

According to an embodiment, the surfactants which are used in the composition include one or more of anionic, cationic, non-ionic, amphoteric and polymeric surfactants. According to an embodiment, the surfactants include dispersing agents, wetting agents and emulsifiers. However, those skilled in the art will appreciate that it is possible to utilize other surfactants without departing from the scope of the present invention. The surfactants are commercially manufactured and available through various companies.

The anionic surfactants include one or more of, but not limited to a salt of fatty acid, a benzoate, a polycarboxylate, a salt of alkylsulfuric acid ester, alkyl ether sulfates, an alkyl sulfate, an alkylaryl sulfate, an alkyl diglycol ether sulfate, a salt of alcohol sulfuric acid ester, an alkyl sulfonate, an alkylaryl sulfonate, an aryl sulfonate, a lignin sulfonate, an alkyldiphenylether disulfonate, a polystyrene sulfonate, a salt of alkylphosphoric acid ester, an alkylaryl phosphate, a styrylaryl phosphate, sulfonate docusates, a salt of polyoxyethylene alkyl ether sulfuric acid ester, a polyoxyethylene alkylaryl ether sulfate, alkyl sarcosinates, alpha olefin sulfonate sodium salt, alkyl benzene sulfonate or its salts, sodium lauroyl sarcosinate, a Sulfosuccinates, polyacrylates, polyacrylates—free acid and sodium salt, salt of polyoxyethylene alkylaryl ether sulfuric acid ester, a polyoxyethylene alkyl ether phosphate, a salt of polyoxyethylene alkylaryl phosphoric acid ester, sulfosuccinates-mono and other diesters, phosphate esters, alkyl naphthalene sulfonate-isopropyl and butyl derivatives, alkyl ether sulfates—sodium and ammonium salts; alkyl aryl ether phosphates, ethylene oxides and its derivatives, a salt of polyoxyethylene aryl ether phosphoric acid ester, mono-alkyl sulphosuccinates, aromatic hydrocarbon sulphonates, 2-acrylamido-2-methylpropane sulfonic acid, ammonium lauryl sulfate, ammonium perfluorononanoate, Docusate, Disodium cocoamphodiacetate, Magnesium laureth sulfate, Perfluorobutanesulfonic acid, Perfluorononanoic acid, carboxylates, Perfluorooctanesulfonic acid, Perfluorooctanoic acid, Phospholipid, Potassium lauryl sulfate, Soap, Soap substitute, Sodium alkyl sulfate, Sodium dodecyl sulfate, Sodium dodecylbenzenesulfonate, Sodium laurate, Sodium laureth sulfate, Sodium lauroyl sarcosinate, Sodium myreth sulfate, Sodium nonanoyloxybenzenesulfonate, Sodium pareth sulfate, alkyl carboxylates, Sodium stearate, alpha olefin sulphonates, Sulfolipid, naphthalene sulfonate salts, alkyl naphthalene sulfonate fatty acid salts, naphthalene sulfonate condensates-sodium salt, fluoro carboxylate, fatty alcohol sulphates, alkyl naphthalene sulfonate condensates-sodium salt, a naphthalene sulfonic acid condensed with formaldehyde or a salt of alkylnaphthalene sulfonic acid condensed with formaldehyde; or salts, derivatives thereof.

Cationic surfactants include one or more of, but not limited to Dialkyl dimethyl ammonium chlorides, Alkyl methyl ethoxylated ammonium chlorides or salts, Dodecyl-, Coco-, Hexadecyl-, Octadecyl-, Octadecyl/Behenyl-, Behenyl-, Cocoamidopropyl-, Trimethyl Ammonium Chloride; Coco-, Stearyl-, bis(2-hydroxyethyl)Methyl Ammonium Chloride, Benzalkonium Chloride, Alkyl-, Tetradecyl-, Octadecyl-Dimethyl Benzyl Ammonium Chloride, Dioctyl-, Di(Octyl-Decyl)-, Didecyl-, Dihexadecyl-Distearyl-, Di(Hydrogenated Tallow)-Dimethyl Ammonium Chloride, Di(Hydrogenated Tallow) Benzyl-, Trioctyl-, Tri(Octyl-Decyl)-, Tridodecyl-, Trihexadecyl-Methyl Ammonium Chloride, Dodecyl Trimethyl-, Dodecyl Dimethyl Benzyl-, Di-(Octyl-Decyl) Dimethyl, Didecyl Dimethyl-Ammonium Bromide, quaternised amine ethoxylates, Behentrimonium chloride, Benzalkonium chloride, Benzethonium chloride, Benzododecinium bromide, Bronidox, quaternary ammonium salts Carbethopendecinium bromide, Cetalkonium chloride, Cetrimonium bromide, Cetrimonium chloride, Cetylpyridinium chloride, Didecyldimethylammonium chloride, Dimethyldioctadecylammonium bromide, Dimethyldioctadecylammonium chloride, Domiphen bromide, Lauryl methyl gluceth-10 hydroxypropyl dimonium chloride, Octenidine dihydrochloride, Olaflur, N-Oleyl-1,3-propanediamine, Pahutoxin, Stearalkonium chloride, Tetramethylammonium hydroxide, Thonzonium bromide; salts or derivatives thereof.

The non-ionic surfactants include one or more of but not limited to polyol esters, polyol fatty acid esters, polyethoxylated esters, polyethoxylated alcohols, ethoxylated and propoxylated fatty alcohols, ethoxylated and propoxylated alcohols, EO/PO copolymers; di, tri-block copolymers; block copolymers of polyethylene glycol and polypropylene glycol, poloxamers, polysorbates, alkyl polysaccharides such as alkyl polyglycosides and blends thereof, amine ethoxylates, sorbitan fatty acid ester, glycol and glycerol esters, glucosidyl alkyl ethers, sodium tallowate, polyoxyethylene glycol, sorbitan alkyl esters, sorbitan derivatives, fatty acid esters of sorbitan (Spans) and their ethoxylated derivatives (Tweens), and sucrose esters of fatty acids, Alkyl polyglycoside, Cetostearyl alcohol, Cetyl alcohol, Cocamide DEA, Cocamide MEA, Decyl glucoside, Decyl polyglucose, Glycerol monostearate, Lauryl glucoside, Maltosides, Monolaurin, Narrow-range ethoxylate, Nonidet P-40, Nonoxynol-9, Nonoxynols, Octaethylene glycol monododecyl ether, N-Octyl beta-D-thioglucopyranoside, Octyl glucoside, Oleyl alcohol, PEG-10 sunflower glycerides, Pentaethylene glycol monododecyl ether, Polidocanol, Poloxamer, Poloxamer 407, Polyethoxylated tallow amine, Polyglycerol polyricinoleate, Polysorbate, Polysorbate 20, Polysorbate 80, Sorbitan, Sorbitan monolaurate, Sorbitan monostearate, Sorbitan tristearate, Stearyl alcohol, Surfactin, glyceryl laureate, lauryl glucoside, nonylphenolpolyethoxyethanols, nonyl phenol polyglycol ether, castor oil ethoxylate, polyglycol ethers, polyadducts of ethylene oxide and propylene oxide, block copolymer of polyalkylene glycol ether and hydroxystearic acid, ethylene oxide propylene oxide block copolymer, tributylphenoxypolyethoxy ethanol, octylphenoxypolyethoxy ethanol, etho-propoxylatedtristyrlphenols, ethoxylated alcohols, polyoxy ethylene sorbitan, a glycerin fatty acid ester, a fatty acid polyglyceride, a fatty acid alcohol polyglycol ether, acetylene glycol, acetylene alcohol, an oxyalkylene block polymer, a polyoxyethylene alkyl ether, a polyoxyethylene alkylaryl ether, a polyoxyethylene styrylaryl ether, a polyoxyethylene glycol alkyl ether, polyethylene glycol, a polyoxyethylene fatty acid ester, a polyoxyethylene sorbitan fatty acid ester, a polyoxyethylene glycerin fatty acid ester, Alcohol ethoxylates—C6 to C16/18 alcohols, linear and branched, Alcohol alkoxylates—various hydrophobes and EO/PO contents and ratios, Fatty acid esters—mono and diesters; lauric, stearic and oleic; Glycerol esters—with and without EO; lauric, stearic, cocoa and tall oil derived, Ethoxylated glycerine, Sorbitan esters—with and without EO; lauric, stearic and oleic based; mono and trimesters, Castor oil ethoxylates—5 to 200 moles EO; non-hydrogenated and hydrogenated, Polyethylene glycol—200, 300, 400, 600, 1450, 3350 and 8000, Methyl capped polyethylene glycol—350 and 550, Block polymers, Alkyl polyglucosides, Amine oxides-ethoxylated and non-ethoxylated; alkyl dimethyl, Fatty amine ethoxylates—coco, tallow, stearyl, oleyl amines, a polyoxyethylene hydrogenated castor oil or a polyoxypropylene fatty acid ester; salts or derivatives, and mixtures thereof.

Amphoteric or Zwitterionic surfactants include one or more of, but not limited to one or more of betaine, coco and lauryl amidopropyl betaines, Coco Alkyl Dimethyl Amine Oxides, alkyl dimethyl betaines; C8 to C18, Alkyl dipropionates-sodium lauriminodipropionate, Cocoamidopropyl hydroxy sulfobetaine, imidazolines, phospholipids phosphatidylserine, phosphatidylethanolamine, phosphatidylcholine, and sphingomyelins, Lauryl Dimethylamine Oxide, alkyl amphoacetates and proprionates, alkyl Ampho(di)acetates, and diproprionates, lecithin and ethanolamine fatty amides; or salts, derivatives thereof.

Surfactants that are commercially available under the trademark but are not limited to Atlas G5000, TERMUL 5429, TERMUL 2510, ECOTERIC®, EULSOGEN® 118, Genapol® X, Genapol® OX-080, Genapol® C100, Emulsogen® EL 200, Arlacel P135, Hypermer 8261, Hypermer B239, Hypermer B261, Hypermer B246sf, Solutol HS 15, Promulgen™ D, Soprophor 7961P, Soprophor TSP/461, Soprophor TSP/724, Croduret 40, Etocas 200, Etocas 29, Rokacet R26, Cetomacrogol 1000, CHEMONIC OE-20, Triton N-101, Triton X-100, Tween 20, 40, 60, 65, 80, Span20, 40, 60, 80, 83, 85, 120, Brij®, Atlox 4912, Atlas G5000, TERMUL 3512, TERMUL 3015, TERMUL 5429, TERMUL 2510, ECOTERIC®, ECOTERIC® T85, ECOTERIC® T20, TERIC12A4, EULSOGEN® 118, Genapol®X, Genapol®OX-080, Genapol® C100, Emulsogen® EL 200, Arlacel P135, Hypermer 8261, Hypermer B239, Hypermer B261, Hypermer B246sf, Solutol HS 15, Promulgen™ D, Soprophor 7961P, Soprophor TSP/461, Soprophor TSP/724, Croduret 40, Etocas 200, Etocas 29, Rokacet R26, CHEMONIC OE-20, Triton™ N-101, IGEPAL CA-630 and Isoceteth-20.

According to an embodiment, the surfactants are present in an amount of 0.1% to 95% w/w of the total composition. According to an embodiment, the surfactants are present in an amount of 0.1% to 85% w/w of the total composition. According to an embodiment, the surfactants are present in an amount of 0.1% to 75% w/w of the total composition. According to an embodiment, the surfactants are present in an amount of 0.1% to 60% w/w of the total composition. According to an embodiment, the surfactants are present in an amount of 0.1% to 50% w/w of the total composition. According to an embodiment, the surfactants are present in an amount of 0.1% to 40% w/w of the total composition. According to an embodiment; the surfactants are present in an amount of 0.1% to 30% w/w of the total composition. According to a further embodiment, the surfactants are present in an amount of 0.1% to 20% w/w of the total composition. According to an embodiment, the surfactants are present in an amount of 0.1% to 10% w/w of the total composition. According to an embodiment, the surfactants are present in an amount of 0.1% to 5% w/w of the total composition.

According to an embodiment, the disintegrating agents is selected from, but not limited to one or more of inorganic water soluble salts e.g. sodium chloride, nitrate salts; water soluble organic compounds such as urea, agar, hydroxypropyl starch, carboxymethyl starch ether, tragacanth, gelatin, casein, microcrystalline cellulose, cross-linked sodium carboxymethyl cellulose, carboxymethyl cellulose, carboxymethyl cellulose calcium, sodium tripolyphosphate, sodium hexametaphosphate, metal stearates, a cellulose powder, dextrin, methacrylate copolymer, Polyplasdone® XL-10 (crosslinked polyvinylpyrrolidone), poly(vinylpyrrolidone), polyaminocarboxylic acid chelate compound, sulfonated styrene-isobutylene-maleic anhydride copolymer, salts of polyacrylates of methacrylates, starch-polyacrylonitrile graft copolymer, sodium or potassium bicarbonates/carbonates or their mixtures or salts with acids such as citric and fumaric acid, or salts, derivatives or mixtures thereof. However, those skilled in the art will appreciate that it is possible to utilize different disintegrating agents without departing from the scope of the present invention. The disintegrating agents are commercially manufactured and available through various companies. According to an embodiment, the disintegrating agents are present in the amount of 0.1% to 50% w/w of the composition. According to further embodiment disintegrating agents are present in the amount of 0.1% to 40% w/w of the composition. According to further embodiment disintegrating agents are present in the amount of 0.1% to 30% w/w of the composition. According to further embodiment disintegrating agents are present in the amount of 0.1% to 20% w/w of the composition. According to further embodiment disintegrating agents are present in the amount of 0.1% to 10% w/w of the composition. According to further embodiment disintegrating agents are present in the amount of 0.1% to 5% w/w of the composition.

According to an embodiment, the binding agent or binder which are used in the algal composition can be at least one of proteins; lipoproteins; lipids, glycolipid, glycoprotein, carbohydrates such as monosaccharides, disaccharides, oligosaccharides and polysaccharides; complex organic substance, synthetic organic polymers or derivatives and combinations thereof.

According to an embodiment, the binder is a carbohydrate. The carbohydrate binders include one or more of glucose, mannose, fructose, galactose, sucrose, lactose, maltose, xylose, arabinose, sorbitol, mannitol, trehalose, Raffinose, stachyose, fructo-oligosaccharides, Amylose, amylopectin, modified starches, Cellulose, hemicellulose, hydrocolloids or mixtures thereof. The binding agents also include corn syrup; celluloses such as carboxymethyl cellulose, ethyl cellulose, hydroxyethyl cellulose, hydroxymethylethyl cellulose, hydroxyethylpropyl cellulose, methyl hydroxyethyl cellulose, methyl cellulose; starches such as amylose, seagel, starch acetates, starch hydroxyethyl ethers, ionic starches, long-chain alkyl starches, dextrins, maltodextrin, amine starches, phosphates starches, and dialdehyde starches; plant starches such as corn starch and potato starch; other carbohydrates such as pectin, amylopectin, xylan, xanthan gum, glycogen, agar, gluten, alginic acid, phycocolloids, gum arabic, guar gum, gum karaya, gum tragacanth and locust bean gum.

The binding agents or binder also include complex organic substances such as phenyl naphthalene sulphonate, lignin and nitrolignin; derivatives of lignin such as lignosulfonate salts illustratively including calcium lignosulfonate and sodium lignosulfonate and complex carbohydrate-based compositions containing organic and inorganic ingredients such as molasses.

The binding agents also include synthetic organic polymers such as ethylene oxide polymers or copolymers, propylene oxide copolymer, polyethylene glycols, polyethylene oxides, polyacrylamides, polyacrylates, polyvinyl pyrrolidone, polyalkyl pyrrolidone, polyvinyl alcohol, polyvinylmethyl ether, polyvinyl acrylates, poly(vinyl acetate), sodium polyacrylate, polylactic acid, polyethoxylated fatty acids, polyethoxylated fatty alcohols, latex and phospholipid (for example, cephalin, lecithin and the like) or salts, derivatives thereof. However, those skilled in the art will appreciate that it is possible to utilize different binding agents without departing from the scope of the present invention.

According to further embodiment, the protein binders are selected based on solubility and include one or more selected from simple proteins, conjugated proteins or derived proteins, water soluble proteins, acidic proteins, basic proteins, water insoluble proteins, or derivatives thereof.

According to further embodiment, the suitable protein binders can include one or more of Albumin, Histone, Protamine, Prolamine, Albuminoids, Phosphoprotein, Mucoprotein, Chromoprotein, Lactose, Proteinase, Pyruvate dehydrogenase, Ribonuclease, flavoprotein, Cytochrome C, Cerruloplasmin, Myoglobin, Lysozyme, Proteoses, Peptones, Chymotrypsin, Cytochromo C; Lactate dehydrogenase, Subtilisin, Trypsin, Actin, Myosin, Ricin, Lectin, Collagen, Fibroin, Adrenalin, Elastin; Soy extract, Zein; Ovalbumin and Gamma globulin or derivatives thereof. However, those skilled in the art will appreciate that it is possible to utilize different binding agents without departing from the scope of the present invention.

The binding agents are commercially manufactured and available through various companies.

According to further embodiment binding agent is present in the amount of 0.1% to 20% w/w of the composition. According to further embodiment binding agent is present in the amount of 0.1% to 10% w/w of the composition. According to further embodiment binding agent is present in the amount of 0.1% to 5% w/w of the composition.

According to an embodiment, the carriers which are used in the algal composition include, but are not limited to one or more of solid carriers or fillers or diluents. According to another embodiment, the carriers can be mineral carriers, plant carriers, synthetic carriers, water-soluble carriers. However, those skilled in the art will appreciate that it is possible to utilize different carriers without departing from the scope of the present invention. The carriers are commercially manufactured and available through various companies.

The solid carriers include natural minerals like clay such as china clay, acid clay, kaolin such as kaolinite, dickite, nacrite, and halloysite, serpentines such as chrysotile, lizardite, antigorite, and amesite, synthetic and diatomaceous silicas, montmorillonite minerals such as sodium montmorillonite, calcium montmorillonite, and magnesium montmorillonite, smectites, such as saponite, hectorite, sauconite, and hyderite, micas, such as pyrophyllite, talc, agalmatolite, muscovite, phengite, sericite, and illite, silicas such as cristobalite and quartz, hydrated magnesium silicates, such as attapulgite and sepiolite; calcium carbonates, such as dolomite and calcium carbonate fine powder, sulfate minerals, such as gypsum, tuff, vermiculite, laponite, pumice, bauxite, hydrated aluminas, calcined alumina, perlite, sodium bicarbonate, volclay, vermiculites, limestone, natural and synthetic silicates e.g. calcium and magnesium silicates; titanium dioxide, hydroxides, silicates, carbonates or sulfates of calcium, magnesium, aluminum and titanium; oxides of aluminum, titanium, magnesium, calcium and zinc, charcoal, silicas, wet process silicas, dry process silicas, calcined products of wet process silicas, surface-modified silicas, mica, zeolite, diatomaceous earth, calcined aluminas, derivatives thereof; chalks (Omya®), fuller's earth, loess, mirabilite, white carbon, slaked lime, inorganic salts such as ammonium sulfate, sodium sulfate, potassium chloride, potassium and barium sulphates or derivatives thereof; synthetic silicic acid, starch, modified starch (Pineflow, available from Matsutani Chemical industry Co., Ltd.), cellulose, sulfur powder, urea powder, plant carriers such as cellulose, chaff, wheat flour, wood flour, starch, rice bran, wheat bran, and soybean flour, tobacco powder, a vegetable powder polyethylene, polypropylene, poly(vinylidene chloride), methyl cellulose, hydroxypropyl cellulose, hydroxypropyl methylcellulose, sodium carboxymethyl cellulose, propylene glycol alginate, polyvinylpyrrolidone, carboxyvinyl polymer, casein sodium, sucrose, sodium chloride, salt cake, potassium pyrophosphate, sodium tripolyphosphate, maleic acid, fumaric acid, and malic acid or derivatives or mixtures thereof. Commercially available Silicates are Aerosil brands, Sipemat brands as Sipernat® 50S and CALFLO E, and kaolin 1777. However, those skilled in the art will appreciate that it is possible to utilize different solid carriers without departing from the scope of the present invention. The solid carriers are commercially manufactured and available through various companies.

However, those skilled in the art will appreciate that it is possible to utilize different carriers without departing from the scope of the present invention. According to an embodiment carrier is present in the amount of 0.1% to 98% w/w of the composition. According to further embodiment carrier is present in the amount of 0.1% to 80% w/w of the composition. According to further embodiment carrier is present in the amount of 0.1% to 60% w/w of the composition. According to further embodiment carrier is present in the amount of 0.1% to 40% w/w of the composition. According to further embodiment carrier is present in the amount of 0.1% to 20% w/w of the composition. According to further embodiment carrier is present in the amount of 0.1% to 10% w/w of the composition. According to further embodiment carrier is present in the amount of 0.1% to 5% w/w of the composition.

According to an embodiment, the coating agents include binders, carriers or fillers or mixtures thereof which have been disclosed herein above in the specification.

According to an embodiment, the anticaking agents which are used in the algal composition include, but are not limited to one or more of polysaccharides such as starch, alginic acid, mannose, galactose; poly(vinylpyrrolidone), fumed silica (white carbon), ester gum, a petroleum resin, Foammaster® Soap L sodium stearate, Brij® 700 polyoxyethylene (100) stearyl ether, Aerosol® OT-B sodium dioctyl sulfosuccinate, Silwet® L-77 silicone-polyether copolymer, sodium and ammonium phosphates, sodium acetate, sodium metasilicate, magnesium, zinc and calcium sulfates, magnesium hydroxide, anhydrous calcium chloride, sodium alkylsulfosuccinates, calcium and barium oxides, sodium carbonate or bicarbonate, salts or derivatives thereof. However, those skilled in the art will appreciate that it is possible to utilize different anti caking agents without departing from the scope of the present invention. The anti caking agents are commercially manufactured and available through various companies.

According to an embodiment, the antifoaming agents or defoamers which are used in the algal composition include, but not limited to one or more of silica, siloxane, silicone dioxide, polydimethyl siloxane, alkyl polyacrylates, ethylene oxide/propylene oxide copolymers, polyethylene glycol, Silicone oils and magnesium stearate or derivatives thereof. Preferred antifoaming agents include silicone emulsions (such as, e.g., Silikon® SRE, Wacker or Rhodorsil® from Rhodia), long-chain alcohols, fatty acids, fluoroorganic compounds. However, those skilled in the art will appreciate that it is possible to utilize different antifoaming agents without departing from the scope of the present invention. The antifoaming agents are commercially manufactured and available through various companies.

According to an embodiment, the pH-adjusters or buffers or neutralizing agents which are used in the algal composition include both acids and bases of the organic or inorganic type and mixtures thereof. According to further embodiment, pH-adjusters or buffers or neutralizing agents include, but not limited to organic acids, inorganic acids and alkali metal compounds or salts, derivatives thereof. According to an embodiment, the organic acids include, but not limited to one or more of citric, malic, adipic, fumaric, maleic, succinic, and tartaric acid, or salts, derivatives thereof; and the mono-, di-, or tribasic salts of these acids or derivatives thereof. Suitable salts of these acids be the soluble or meltable salts and include those salts in which one or more acidic protons are replaced with a cation such as sodium, potassium, calcium, magnesium, and ammonium and mixtures thereof. Alkali metal compounds can include hydroxides of alkali metals such as sodium hydroxide and potassium hydroxide, carbonates of alkali metals such as sodium carbonate, magnesium carbonates and potassium carbonate, hydrogencarbonates of alkali metals such as sodium hydrogencarbonate and alkali metal phosphates such as sodium phosphate and mixtures thereof. According to an embodiment, the salts of inorganic acids include, but not limited to one or more of alkali metal salts such as lithium chloride, sodium chloride, potassium chloride, lithium nitrate, sodium nitrate, potassium nitrate, lithium sulfate, sodium sulfate, potassium sulfate, sodium monohydrogen phosphate, potassium monohydrogen phosphate, sodium dihydrogen phosphate, potassium dihydrogen phosphate and the like; alkaline earth metal salts such as magnesium chloride, calcium chloride, magnesium nitrate, calcium nitrate, magnesium sulfate and the like; and ammonium salts such as ammonium chloride, ammonium sulfate, ammonium monohydrogen phosphate, ammonium dihydrogen phosphate and the like. Preferred salts for use in this invention include sodium chloride, potassium chloride, calcium chloride and magnesium sulfate. Mixtures can also be used to create a pH-adjusters or buffers or neutralizing agents. However, those skilled in the art will appreciate that it is possible to utilize different pH-adjusters or buffers or neutralizing agents without departing from the scope of the present invention. The pH-adjusters or buffers or neutralizing agents are commercially manufactured and available through various companies.

According to an embodiment, the spreading agents which are used in the algal composition include, but not limited to one or more of cellulose powder, dextrin, modified starch, a polyaminocarboxylic acid chelate compound, crosslinked poly(vinylpyrrolidone), a copolymer of maleic acid with a styrene compound, a (meth)acrylic acid copolymer, a half ester of a polymer consisting of polyhydric alcohol with dicarboxylic anhydride, a water-soluble salt of polystyrenesulfonic acid, fatty acids, latex, aliphatic alcohols, vegetable oils such as cottonseed, or inorganic oils, petroleum distillates, modified trisiloxanes, polyglycol, polyethers, clatharates or salts or derivatives thereof. However, those skilled in the art will appreciate that it is possible to utilize different spreading agents without departing from the scope of the present invention. The spreading agents are commercially manufactured and available through various companies.

According to an embodiment, the sticking agents which are used in the algal composition include, but not limited to one or more of paraffin, a polyamide resin, polyacrylate, polyoxyethylene, wax, polyvinyl alkyl ether, an alkylphenol-formalin condensate, fatty acids, latex, aliphatic alcohols, vegetable oils such as cottonseed, or inorganic oils, petroleum distillates, modified trisiloxanes, polyglycol, polyethers, clatharates, a synthetic resin emulsion or salts or derivatives thereof. However, those skilled in the art will appreciate that it is possible to utilize different sticking agents without departing from the scope of the present invention. The sticking agents are commercially manufactured and available through various companies.

According to an embodiment, the stabilizers which are used in the algal composition include, but not limited to one or more of peroxide compounds such as hydrogen peroxide and organic peroxides, alkyl nitrites such as ethyl nitrite and alkyl glyoxylates such as ethyl glyoxylate, zeolite, calcined lime and magnesium oxide; antioxidants such as phenol compounds, amine compounds, sulfur compounds, phosphoric acid compounds and the like; ultraviolet absorbers such as salicylic acid compounds, benzophenone compounds or derivatives thereof; alkaline earth and transition metal sulfates such as magnesium, zinc, aluminum and iron, sodium hexametaphosphate, lithium, sodium and potassium phosphates, sodium pyrophosphate, calcium chloride, oxide and boric anhydride or derivatives thereof. However, those skilled in the art will appreciate that it is possible to utilize different stabilizers without departing from the scope of the present invention. The stabilizers are commercially manufactured and available through various companies According to an embodiment, the preservatives include but not limited to one or more of bactericides, anti-fungal agents, biocides, anti-microbial agents, and antioxidant. Non limiting examples of preservatives can include one or more of benzoic acid, its esters and salts, para-hydroxybenzoic acid (paraben), its esters and salts, propionic acid and its salts, salicylic acid and its salts, 2,4-hexadienoic acid (sorbic acid) and its salt, formaldehyde and paraformaldehyde, 2-hydroxybiphenyl ether and its salts, 2-zincsulfidopyridine N-oxide, inorganic sulfites and bisulfites, sodium iodate, chlorobutanol, dehydraacetic acid, formic acid, 1,6-bis(4-amidino-2-bromophenoxy)-n-hexane and its salts, 10-undecylenic acid and its salts, 5-amino-1,3-bis(2-ethyl hexyl)-5-methylhexahydropyrimidine, 5-bromo-5-nitro-1,3-dioxane, 2-bromo-2-nitropropane-1,3-diol, 2,4-dichlorobenzyl alcohol, N-(4-chlorophenyl)-N'-(3,4-dichlorophenyl)urea, 4-chloro-m-cresol, 2,4,4'-trichloro-2'-hydroxy diphenyl ether, 4-chloro-3,5-dimethyl phenol, 1,1'-methyl ene-bis(3-(1-hydroxy methyl-2,4-dioximidazolidin-5-yl)urea), poly (hexamethylenediguanide) hydrochloride, 2-phenoxyethanol, hexamethylenetetramine, 1-(3-chloroallyl)-3,5,7-triaza-1-azonia-adamantane chloride, 1(4-chlorophenoxy)-1-(1H-imidazol-1-yl)-3,3-dimethyl-2-butanone, 1,3-bis (hydroxymethyl)-5,5-dimethyl-2,4-imidazolidinedione, benzyl alcohol, octopirox, 1,2-dibromo-2,4-dicyanobutane, 2,2'-methylenebis(6-bromo-4-chlorophenol), bromochlorophene, dichlorophene, 2-benzyl-4-chlorophenol, 2-chloroacetamide, chlorhexidine, chlorhexidine acetate, chlorhexidine gluconate, chlorhexidine hydrochloride, 1-phenoxypropan-2-ol, N-alkyl(C12-C22)trimethylammonium bromide and chloride, 4,4-dimethyl-1,3-oxazolidine, N-hydroxymethyl-N-(1,3-di(hydroxymethyl)-2,5-dioxoimidazolidin-4-yl)-N'-hydroxymethylurea, 1,6-bis(4-amidinophenoxy)-n-hexane and its salts, glutaraldehyde, 5-ethyl-1-aza-3,7-dioxabicyclo(3.3.0)octane, 3-(4-chlorophenoxy) propane-1,2-diol, Hyamine, alkyl(C8-C18) dimethylbenzylammonium chloride, alkyl(C8-C18) dimethylbenzylammonium bromide, alkyl(C8-C18)

dimethylbenzylammonium saccharinate, benzyl hemiformal, 3-iodo-2-propynyl butylcarbamate, sodium hydroxymethylaminoacetate, cetyltrimethylammonium bromide, cetylpyridinium chloride, and derivatives of 2H isothiazol-3-one (so-called isothiazolone derivatives) such as alkylisothiazolones (for example 2-methyl-2H-isothiazol-3-one, MIT; chloro-2-methyl-2H-isothiazol-3-one, CIT), benzoisothiazolones (for example 1,2-benzoisothiazol-3(2H)-one, BIT, commercially available as Proxel® types from ICI) or 2-methyl-4,5-trimethylene-2H-isothiazol-3-one (MTIT), propionic acid, C1-C4-alkyl para-hydroxybenzoate, an dichlorophene, Proxel® from ICI or Acticide® RS from Thor Chemie and Kathon® MK from Rohm & Haas, Bacto-100, thimerosal, Sorbic Acid, Sodium Propinoate, Sodium Benzoate, Propyl Paraben Sodium, Potassium Sorbate, Potassium Benzoate, Phenyl Mercuric Nitrate, Phenyl Ethyl Alcohol, Propyl Paraben, Phenol, Methyl Paraben Sodium, Ethylparaben, Methylparaben, Butylparaben, Chlorobutanol, Bezyla Alcohol, Benzoic Acid, Benzothonium Chloride, Cetylpyridinium Chloride, Benzalkonium Chloride, 1,2-benzothiazol-3-one, Preventol® (Lanxess®), Butylhydroxytoluene, potassium sorbate, iodine-containing organic compounds such as 3-bromo-2,3-diiodo-2-propenyl ethyl carbonate, 3-iodo-2-propynyl butyl carbamate, 2,3,3-triiodo allyl alcohol, and parachlorophenyl-3-iodopropargylformal; benzimidazole compounds and benzthiazole compounds such as 2-(4-thiazolyl)benzimidazole and 2-thiocyanomethylthiobenzo-thiazole; triazole compounds such as 1-(2-(2',4'-dichlorophenyl)-1,3-dioxolane-2-ylmethyl)-1H-1,2,4-triazole, 1-(2-(2',4'-dichloro phenyl)-4-propyl-1,3-dioxolane-2-ylmethyl)-1H-1,2,4-triazole, and α-(2-(4-chlorophenyl) ethyl)-α-(1,1-dimethyl ethyl)-1H-1,2,4-triazole-1-ethanol; and naturally occurring compounds such as 4-isopropyl tropolone (hinokitiol) and boraxor salts or derivatives thereof. Antioxidants includes but not limited to one or more of amino acids (e.g. glycine, histidine, tyrosine, tryptophan) and derivatives thereof, imidazole and imidazole derivatives (e.g. urocanic acid), peptides, such as, D,L-carnosine, D-carnosine, L-carnosine and derivatives thereof (e.g. anserine), 4,4'-thiobis-6-t-butyl-3-methylphenol, 2,6-di-t-butyl-p-cresol (BHT), and pentaerythrityl tetrakis[3-(3,5,-di-t-butyl-4-hydroxyphenyl)]propionate; amine antioxidants such as N,N'-di-2-naphthyl-p-phenylenediamine; hydroquinoline antioxidants such as 2,5-di (t-amyl)hydroquinoline; sulfur-containing antioxidants such as dilauryl thiodipropionate; and phosphorus-containing antioxidants such as triphenyl phosphate, carotenoids, carotenes (e.g. α-carotene, β-carotene, lycopene) and derivatives thereof, lipoic acid and derivatives thereof (e.g. dihydrolipoic acid), aurothioglucose, propylthiouracil and further thio compounds (e.g. thioglycerol, thiosorbitol, thioglycolic acid, thioredoxin, glutathione, cysteine, cystine, cystamine and the glycosyl, N-acetyl, methyl, ethyl, propyl, amyl, butyl, lauryl, palmitoyl, oleyl, γ-linoleyl, cholesteryl and glyceryl esters thereof), and salts thereof, dilauryl thiodipropionate, distearyl thiodipropionate, thiodipropionic acid and derivatives thereof (esters, ethers, peptides, lipids, nucleotides, nucleosides and salts), and sulfoximine compounds (e.g. buthionine sulfoximines, homocysteine sulfoximine, buthionine sulfones, penta-, hexa-, heptathionine sulfoximine) in very low tolerated doses (e.g. pmol/kg to pmol/kg), also metal chelating agents (e.g. α-hydroxy fatty acids, EDTA, EGTA, phytic acid, lactoferrin), α-hydroxy acids (e.g. citric acid, lactic acid, malic acid), humic acids, gallic esters (e.g. propyl, octyl and dodecyl gallate), unsaturated fatty acids and derivatives, hydroquinone and derivatives thereof (e.g. arbutin), ubiquinone and ubiquinol, and derivatives thereof, vitamin C and derivatives thereof (e.g. ascorbyl palmitate, stearate, dipalmitate, acetate, Mg ascorbyl phosphates, sodium and magnesium ascorbate, disodium ascorbyl phosphate and sulfate, potassium ascorbyl tocopheryl phosphate, isoascorbic acid and derivatives thereof, vitamin A and derivatives (e.g. vitamin A palmitate), the coniferyl benzoate of benzoin resin, rutin, rutinic acid and derivatives thereof, disodium rutinyl disulfate, dibutylhydroxytoluene, 4,4-thiobis-6-tert-butyl-3-methylphenol, butylhydroxy anisole, p-octylphenol, mono-(di- or tri-) methyl benzylphenol, 2,6-tert-butyl-4-methylphenol, pentaerythritol-tetrakis 3-(3,5-di-tert-butyl-4-hydroxyphenyl) propionate, butylhydroxytoluene, butylhydroxyanisol, nordihydroguaiacic acid, nordihydroguaiaretic acid, trihydroxybutyrophenone, uric acid and derivatives thereof, mannose and derivatives thereof, selenium and selenium derivatives (e.g. selenomethionine), stilbenes and stilbene derivatives (e.g. stilbene oxide, trans-stilbene oxide). However, those skilled in the art will appreciate that it is possible to utilize different preservatives without departing from the scope of the present invention. The preservatives are commercially manufactured and available through various companies.

According to an embodiment, the preservative or bactericides or anti-fungal agents or biocides or anti-microbial agents or antioxidant is present in the amount of 0.1% to 20% w/w. According to further embodiment, the preservative or bactericides or anti-fungal agents or biocides or anti-microbial agents or antioxidant is present in the amount of 0.1% to 10% w/w of the total composition. According to further embodiment, the preservative or bactericides or anti-fungal agents or biocides or anti-microbial agents or antioxidant is present in the amount of 0.1% to 5% w/w of the total composition. According to further embodiment, the preservative or bactericides or anti-fungal agents or biocides or anti-microbial agents or antioxidant is present in the amount of 0.1% to 1% w/w of the total composition.

According to an embodiment, the ultraviolet absorbents are selected from, but are not limited to one or more of 2-(2'-hydroxy-5'-methylphenyl)benzotriazole, 2-ethoxy-2'-ethyloxazalic acid bisanilide, succinic acid dimethyl-1-(2-hydroxyethyl)-4-hydroxy-2,2,6,6-tetramethylpiperidine polycondensate, benzotriazole compounds such as 2-(2'-hydroxy-5'-methylphenyl)benzotriazole and 2-(2'-hydroxy-4'-n-octoxyphenyl)benzotriazole; benzophenone compounds such as 2-hydroxy-4-methoxybenzophenone and 2-hydroxy-4-n-octoxybenzophenone; salicylic acid compounds such as phenyl salicylate and p-t-butylphenyl salicylate; 2-ethylhexyl 2-cyano-3,3-diphenyl acrylate, 2-ethoxy-2'-ethyl oxalic bisanilide, and dimethyl succinate-1-(2-hydroxyethyl)-4-hydroxy-2,2,6,6-tetramethylpiperidine polycondensator derivatives or the like. However, those skilled in the art will appreciate that it is possible to utilize different ultraviolet absorbents, without departing from the scope of the present invention. Such ultraviolet absorbents are commercially manufactured and available through various companies.

According to an embodiment, the UV ray scattering agents include titanium dioxide or the like may be used. However, those skilled in the art will appreciate that it is possible to utilize different UV ray scattering agents, without departing from the scope of the present invention. Such UV ray scattering agents are commercially manufactured and available through various companies.

According to an embodiment, the water dispersible granular algal composition further comprises at least one microbe. The microbes include fungi, bacteria or bacteriospores, yeast, viruses, etc. The microbes are commercially developed and manufactured and available through various suppliers around the world.

According to an embodiment, microbes can be present in the amount of 0.1% to 50% w/w of the composition. According to further embodiment microbes can be present in the amount of 0.1% to 40% w/w of the composition. According to further embodiment microbes can be present in the amount of 0.1% to 30% w/w of the composition. According to further embodiment microbes can be present in the amount of 0.1% to 20% w/w of the composition. According to further embodiment microbes can be present in the amount of 0.1% to 15% w/w of the composition. According to further embodiment microbes can be present in the amount of 0.1% to 10% w/w of the composition.

According to an embodiment, the bacteriospores include spores of one or more of *Agrobacterium radiobacter, Azotobacter chroococcum, Azospirillum lippoferum, Azospirillum brasilense, Azospirillum lipoferum, Azospirillum irakense, Azospirillum halopraeferens, Bacillus amyloliquifaciens, Bacillus altitudinis Bradyrhizobium japonicum, Bradyrhizobium elkanii, Bacillus acidiceler, Bacillus acidicola, Bacillus acidiproducens, Bacillus aealius, Bacillus aerius, Bacillus aerophilus, Bacillus agaradhaerens, Bacillus aidingemis, Bacillus akibai, Bacillus alcalophilm, Bacillus altitudmis, Bacillus algicola, Bacillus azotoformans, Bacillus badius, Bacillus atyabhaltai, Bacillus asahti, Bacillus atrophaem, Bacillus cohnii, Bacillus coagulam, Bacillus coahuilemls Bacillus flexus, Bacillus firmus, Bacillus pseudofirmus, Bacillus thuringenesis, Bacillus subtillus, Bacillus aizawai, Bacillus cereus, Bacillus circulans, B. circuians, Bacillus thermolactis, Bacillus kurstaki, Bacillus lentimorbus, Bacillus licheniformis, Bacillus megaterium, Bacillus mycoides, Bacillus mojavensis Bacillus mucillagenosus, Bukholderia cepacia, Bacillus horii, Bacillus humi, Bacillus polygoni, Bacillus popillae, Bacillus pumilus, Bacillus sphaericus, Bacillus neahonii, Bacillus mizhmtemis, Bacillus niabensis, Bacillus macirti, Bacillus polymyxa, Bacillus sonoremis, Bacillus sporothenrnxlura, Bacillus sfratosphericus, Bacillus subierraneus, Bacillus taeamis, Bacillus tequilemis, Bacillus fhermamarcticm, Bacillus thermoamyhvorans, Bacillus thermacloacae, Bacillus thermolactis, Bacillus ihioparans, Pesudomonas fluorescens, Pseudomonas solanacearum, Pseudomonas syringae, Pseudomonas cepacia, Agrobacterium radiobacter, Azotobacter chroococcum Azospirillum lippoferum, Peaenibacillus azotofixans, Peaenibacillus durum, Pasteuria penetrans. Rhizobium leguminosarum, Rhizobium tropici, Bukholderia cepacia, Streptomyces lydicus, Thiobacillus thiooxidans* and *Thiobacillus novellus*. However, those skilled in the art will appreciate that it is possible to use different bacteriospores without departing from the scope of the present invention. The bacteriospores are commercially manufactured and available through various companies.

According to an embodiment the water dispersible granular composition can comprise at least about $1\times10^5$, $2.5\times10^5$, $5\times10^5$, $7.5\times10^5$, $1\times10^6$, $2.5\times10^6$, $5\times10^6$, $7.5\times10^6$, $1\times10^7$, $2.5\times10^7$, $5\times10^7$, $7.5\times10^7$, $1\times10^8$, $2.5\times10^8$, $5\times10^8$, $7.5\times10^8$, $1\times10^9$, $2.5\times10^9$, $5\times10^9$, $7.5\times10^9$, colony forming units (cfu) of the one or more microbes per gram of the composition.

According to an embodiment, the agricultural granular algal composition further comprise one or more of pesticidal actives, water soluble or water insoluble fertilizers, macronutrients and micronutrients and biostimulants.

According to an embodiment, the pesticidal actives include an antifoulant, an insecticide, a fungicide, a herbicide, a nematicide, a pheromone, a defoliant, an acaricide, a plant growth regulator, an algicide, an antifeedant, an avicide, a bactericide, a bird repellent, a biopesticide, a biocide, a chemosterilant, a safener, an insect attractant, an insect repellent, a insect growth regulator, a mammal repellent, a mating disrupter, a disinfectant, a molluscicide, a antimicrobial, a miticide, an ovicide, a fumigant, a plant activator, a rodenticide, a synergist, a virucide, a microbial pesticide, a plant incorporated protectant, other miscellaneous pesticidal active, or salts, derivatives and mixtures therefore.

According to an embodiment, pesticide can be present in the amount of 0.1% to 80% w/w of the composition. According to further embodiment pesticide can be present in the amount of 0.1% to 60% w/w of the composition. According to further embodiment pesticide can be present in the amount of 0.1% to 40% w/w of the composition. According to further embodiment pesticide can be present in the amount of 0.1% to 20% w/w of the composition. According to further embodiment pesticide can be present in the amount of 0.1% to 10% w/w of the composition. According to further embodiment pesticide can be present in the amount of 0.1% to 5% w/w of the composition.

According to another embodiment, the fertilizers can include single nutrient fertilizers, multi nutrient fertilizers, binary fertilizers, compound fertilizers, organic fertilizers or mixtures thereof. However, those skilled in the art will appreciate that it is possible to utilize other fertilizers known in the art, without departing from the scope of the invention.

According to yet another embodiment, the fertilizer can comprise one or more of water soluble fertilizer or water insoluble fertilizer, or salt or complex or derivative, or mixtures thereof.

According to further embodiment, the fertilizers can include, nitrogen, phosphate, potash, ammonia, ammonium nitrate, urea, sodium nitrate, potassium chloride, potassium sulfate, potassium carbonate, potassium nitrate, monoammonium phosphate, diammonium phosphate, calcium ammonium nitrate, super phosphates, phosphogypsum, triple super phosphates, NPK fertilizers or salt or complex or derivative, sulphur based fertilizers, or mixtures thereof. However, the above list of fertilizers is exemplary and not meant to limit the scope of the invention. Those skilled in the art will appreciate that it is possible to use other fertilizers without departing from the scope of the present invention. The fertilizers are commercially manufactured and available through various companies.

According to still further embodiment, the nitrogen fertilizer can include urea, ammonium sulphate, ammonium nitrate, anhydrous ammonia, ammonium nitrate sulphate, Diammonium phosphate, Nitrogen solutions, Monoammonium phosphate, Ammonium polyphosphate, Triple superphosphate or their derivative, oxide or salt or mixtures thereof. However, the above list of nitrogen fertilizers is exemplary and not meant to limit the scope of the invention.

According to still further embodiment, the sulphur based fertilizer can include elemental sulphur, Ammonium thiosulfate, Calcium sulphate, Gypsum or derivative or oxide or salt or mixtures thereof. However, the above list of sulphur based fertilizers is exemplary and not meant to limit the scope of the invention.

According to an embodiment, the water insoluble fertilizer can be one or more of nitrogen, phosphorous, potassium fertilizers or sulphur fertilizers, such as elemental sulphur.

According to an embodiment, fertilizer can be present in the amount of 0.1% to 85% w/w of the composition. According to further embodiment, fertilizer can be present in the amount of 0.1% to 60% w/w of the composition. According to further embodiment, fertilizer can be present in the amount of 0.1% to 40% w/w of the composition. According to further embodiment, fertilizer can be present in the amount of 0.1% to 20% w/w of the composition. According to further embodiment, fertilizer can be present in the amount of 0.1% to 5% w/w of the composition.

According to another embodiment, the micronutrient can comprise one or more of zinc, boron, calcium, magnesium, iron, copper, manganese, silicon, cobalt, chlorine, sodium, molybdenum, chromium, vanadium, selenium, nickel, iodine, Chloride, Fluoride, Phosphorous, Potassium, in their elemental form, or salt, complex or derivative or mixtures thereof. The micronutrient can also comprise one or more of vitamins, organic acids or salt, complex or derivative or mixtures thereof. However, the above list of micronutrients is exemplary and not meant to limit the scope of the invention. Those skilled in the art will appreciate that it is possible to use other micronutrients without departing from the scope of the present invention. The micronutrients are commercially manufactured and available through various companies.

According to further embodiment, the micronutrients can be present in chelated or non-chelated form.

According to still further embodiment, the salts, derivatives, complexes of micronutrients that can be used in the composition can comprise one or more of hydrated Zinc Sulphate, Zinc Oxide, Zinc Chelate, Zinc oxysulfate, Zinc carbonate, Zinc nitrate, Disodium Zinc EDTA, ammoniated zinc sulphate, Zinc molybdate, Sodium Zinc HEDTA, Zinc polyflavonoid, Zinc lignosulphonate, Zinc chloride, Zinc phosphate, Eugenol chelated Zinc, zinc polyflavonoid, Ammoniated zinc sulphate, Hydroxy ethylene di amine triacetic acid (HEDTA), Nitrilo-triacetic acid (NTA) Zinc chelate, Zinc glucoheptonate, Zinc phenolate, Zinc-EDDHA, Zinc glycine, Zinc carbohydrate, Zinc sucrate, Zinc polyamine, Zinc phosphate, Zinc acetate, Zinc gluconate, Boron carbide, Boron nitride, Boric acid, Aluminum oxide, Aluminum dodecaboride, aluminum hydroxide, bauxite, calcitic limestone, Calcium oxalate, Chromium oxide, Cobalt oxide, Cobalt sulphide, Cobalt molybdate, Cobalt carbonate, Copper oxalate, Copper oxide, Copper Sulphide, Copper hydroxide, Cupric sulphide, Copper phosphate, Copper molybdate, Fluorine oxide, Fluorine molybdate, Iron oxide, Iron chelate, Iron sulphide, Magnesium oxide, Magnesium hydroxide, Magnesium phosphate tribasic, Magnesium molybdate, Magnesium carbonate, Manganese oxide, Manganese molybdate, Molybdenum acetate, Molybdenum disulphide, Selenium sulphide, Silicon nitride, Zinc phosphate, basic slag, chromium phosphate, iron sucrate, cobalt phosphide, cobalt cyanide, nickel oxide, nickel oxyhydroxide, nickel carbonate, nickel chromate, nickel hydroxide, millerite, nickel selenide, nickel phosphide, elemental copper, insoluble copper cyanide, chalcocite, copper selenide, copper phosphide, covellite, copper arsenate, elemental silver, zinc chromate, zinc pyrophosphate, tin hydroxide, tin oxide and tin sulfide, or salt or complex or derivative or mixtures thereof. However, those skilled in the art will appreciate that it is possible to use different salt, complex, derivative of micronutrients without departing from the scope of the present invention. These are commercially manufactured and available through various companies.

According to an embodiment, micronutrient can be present in the amount of 0.1% to 85% w/w of the composition. According to further embodiment, micronutrient can be present in the amount of 0.1% to 60% w/w of the composition. According to further embodiment, micronutrient can be present in the amount of 0.1% to 40% w/w of the composition. According to further embodiment, micronutrient can be present in the amount of 0.1% to 20% w/w of the composition.

According to further embodiment, vitamin can comprise one or more of Vitamin A, Vitamin B, Vitamin C, Vitamin D, Vitamin E, Vitamin K, Carotenoids, or derivatives, or salt or complex, derivative or mixtures thereof. However, the above list of vitamins is exemplary and not meant to limit the scope of the invention. Those skilled in the art will appreciate that it is possible to use other vitamins without departing from the scope of the present invention. The vitamins are commercially manufactured and available through various companies.

According to an embodiment, the biostimulants can include one or more of, enzymes, humic acid and fulvic acid. The biostimulants used, are commercially manufactured and available from various manufacturers. However, those skilled in the art will appreciate that it is possible to utilize different biostimulants without departing from the scope of the present invention.

The water dispersible granular algal composition of the invention in contact with an aqueous medium, disintegrate immediately to release the material, and remain dispersed and suspended uniformly throughout the aqueous medium.

Dispersibility of the granular algal formulation is a measure of percent dispersion. Dispersibility is calculated by the minimum percent dispersion. Dispersibility is defined as the ability of the granules to disperse upon addition to a liquid such as water or a solvent. To determine dispersibility of the granular composition as per the standard CIPAC test, MT 174, a known amount of the granular composition was added to a defined volume of water and mixed by stirring to form a suspension. After standing for a short period, the top nine-tenths are drawn off and the remaining tenth dried and determined gravimetrically. The method is virtually a shortened test of suspensibility and is appropriate for establishing the ease with which the granular composition dispersed uniformly in water.

According to an embodiment, the water dispersible granules have a dispersibility of at least 50%. According to an embodiment, the water dispersible granules have a dispersibility of at least 60%. According to an embodiment, the water dispersible granules have a dispersibility of at least 70%. According to an embodiment, the water dispersible granules have a dispersibility of at least 80%. According to an embodiment, the water dispersible granules have a dispersibility of at least 90%. According to an embodiment, the water dispersible granules have a dispersibility of at least 99%. According to an embodiment, the water dispersible granules have a dispersibility of 100%.

According to an embodiment, the water dispersible granules of algal composition exhibit good suspensibility. Suspensibility is defined as the amount of active ingredient (Algae) suspended after a given time in a column of liquid, of stated height, expressed as a percentage of the amount of active ingredient in the original suspension. The water dispersible granules can be tested for suspensibility as per the CIPAC Handbook, "MT 184 Test for Suspensibility" whereby a suspension of known concentration of the granular composition in CIPAC Standard Water was prepared and placed in a prescribed measuring cylinder at a constant temperature, and allowed to remain undisturbed for a specified time. The top 9/10ths were drawn off and the remaining 1/10th was then assayed either chemically, gravimetrically, or by solvent extraction, and the suspensibility was calculated.

According to an embodiment, the water dispersible granules have a suspensibility of at least 40%. According to an embodiment, the water dispersible granules have a suspensibility of at least 50%. According to an embodiment, the water dispersible granules has a suspensibility of at least 60%. According to an embodiment, the water dispersible granules have a suspensibility of at least 70%. According to an embodiment, the water dispersible granules have a suspensibility of at least 80%. According to an embodiment, the water dispersible granules have a suspensibility of at least 90%. According to an embodiment, the water dispersible granules have a suspensibility of at least 99%. According to an embodiment, the water dispersible granules have a suspensibility of 100%

According to an embodiment, the algal granules have a particle size in the range of 0.1 microns to 60 microns. According to further embodiment, the algal granules have a particle size in the range of 0.1 microns to 50 microns. According to further embodiment, the algal granules have a particle size in the range of 0.1 microns to 20 microns. According to further embodiment, the algal granules have a particle size in the range of 0.1 microns to 12 microns. According to further embodiment, the algal granules have a particle size in the range of 0.1 microns to 8 microns.

According to an embodiment, the water dispersible granular algal composition of the invention exhibits superior flowability. The flowability of the granules has been measured in terms of angle of repose. Angle of repose is a characteristic related to interparticulate friction and resistance to movement between particles. The water dispersible granules can be tested for angle of repose as per US Pharmacopoeia-USP 1174 whereby, a symmetrical cone of the material is formed on fixed base with a retaining lip to retain a layer of material on the vibration free base and the height of the funnel is varied as the pile forms. The funnel height should be maintained approximately 2-4 cm from the top of the material pile. The angle of repose is determined by measuring the height of the cone of powder and calculating the angle of repose, a, from the equation: $\tan(\alpha)=\text{height}/0.5$ base. According to an embodiment, the water dispersible granular composition of the invention exhibits angle of repose in the range of 25-40 degrees. According to an embodiment, the water dispersible granular composition of the invention exhibits angle of repose in the range of 25-35 degrees. According to an embodiment, the water dispersible granular composition of the invention exhibits angle of repose in the range of 25-30 degrees.

According to an embodiment the invention relates to the water dispersible granular composition comprising at least one algae in a concentration range of at least 0.1% up to 90% by weight; and, at least one agrochemically acceptable excipient; the composition, with particles in a size range of from 0.1 micron to 60 microns; and, where the granules have suspensibility of at least 60%; dispersibility of at least 60% and flowability (angle of repose) in the range of 25-40 degrees.

According to an embodiment the water dispersible granules of the invention has no hardness.

According to an embodiment, the algal granules demonstrates superior stability towards heat, light, temperature and caking. According to further embodiment, the stability exhibited by the algal granular composition is more than 3 years. According to further embodiment, the stability exhibited by the algal granular composition is more than 2 years. According to further embodiment, the stability exhibited by the algal granular composition is more than 1 year. According to further embodiment, the stability exhibited by the algal granular composition is more than 10 months. According to further embodiment, the stability exhibited by the algal granular composition is more than 8 months. According to further embodiment, the stability exhibited by the algal granular composition is more than 6 months. According to further embodiment, the stability exhibited by the algal granular composition is more than 3 months. According to further embodiment, the stability exhibited by the algal granular composition is more than 1 month.

According to an embodiment, the algal granules demonstrate superior stability in terms of suspensibility under accelerated storage condition (ATS). According to an embodiment, the algal granules demonstrate suspensibility of more than 90% under ATS. According to an embodiment, the algal granules demonstrate suspensibility of more than 80% under ATS. According to an embodiment, the algal granules demonstrate suspensibility of more than 70% under ATS. According to an embodiment, the algal granules demonstrate suspensibility of more than 60% under ATS. According to an embodiment, the algal granules demonstrate suspensibility of more than 50% under ATS.

Wettability is the condition or the state of being wettable and can be defined as the degree to which a solid is wetted by a liquid, measured by the force of adhesion between the solid and liquid phases. The wettability of the granular composition was measured using the Standard CIPAC Test MT-53 which describes a procedure for the determination of the time of complete wetting of wettable formulations. A weighed amount of the granular composition was dropped on water in a beaker from a specified height and the time for complete wetting was determined. According to an embodiment, the granular composition has a wettability of less than 5 minutes. According to another embodiment, the granular composition has a wettability of less than 4 minutes. According to another embodiment, the granular composition has a wettability of less than 3 minutes. According to another embodiment, the granular composition has a wettability of less than 2 minutes. According to another embodiment, the granular composition has a wettability of less than 1 minutes. According to another embodiment, the granular composition has a wettability of less than 30 second.

According to another embodiment, the invention relates to the process for preparing the algal granular composition. According to a further embodiment, the invention relate to the process for preparing the algal granular composition comprising at least one alga and at least one agrochemically acceptable excipient. According to further embodiment, the invention relate to the process for preparing the algal composition in the form of dispersible granules. The algal granules is made by various techniques such as spray drying, fluidized bed granulation, extrusion, freeze drying etc.

According to an embodiment the composition is made by spray drying, extrusion or freeze drying.

According to an embodiment, the process of preparing the water dispersible granular composition involves milling a blend of at least one algae and at least one agrochemically acceptable excipient to obtain a slurry or wet mix. The wet mix obtained is then dried to obtain a granule, for instance in a spray dryer, fluid bed dryer or any suitable granulating equipment.

According to another embodiment, the composition can be made by dry milling the algae, excipients including at least one of surfactants, binders or disintegrants, in an air mill or jet mill to obtain desired particle size. Water is added to the dry powder and the mixture is blended to obtain a dough or paste, which is then extruded through an extruder to obtain the granules. The granules can also be form with low melt extrusion.

According to an embodiment, the invention can further relate to the use of the algal granular composition as at least one of a nutrient composition, a plant strengthener composition, a soil conditioner composition, plant fortification, plant protection and a yield enhancer composition.

According to an embodiment, the invention can relate to a method of application of an effective amount of the algal granular composition, wherein the composition is applied to the seeds, seedling, crops, a plant, plant propagation material, locus, parts thereof or to the surrounding soil.

According to an embodiment, the invention further relates to a method of improving the plant health, improving the plant nutrient, fortifying the plant, protecting the plant, enhancing the plant yield, strengthening the plant or conditioning the soil; the method comprising treating at least one of seeds, seedling, crops, a plant, plant propagation material, locus, parts thereof or to the surrounding soil with effective amount of the algal granular composition including at least one alga and at least one agrochemically acceptable excipient.

According to an embodiment, the invention further relates to a method of fortification of the crops or the plant. The method involves application of the water dispersible granular composition including at least one algae in a concentration range of at least 0.1% up to 90% by weight; and, at least one agrochemically acceptable excipient; the composition having particles in a size range of from 0.1 micron to 60 microns; and, where the granules have suspensibility of at least 60%; dispersibility of at least 60% and flowability (angle of repose) in the range of 25-40 degrees to one or more of the plant, foliage of the plant, plant propagation material, locus of the plant or the plant propagation material, seeds, seedlings, soil and surroundings of the crop.

The composition is applied through a variety of methods. Methods of applying to the soil includes any suitable method, which ensures that the composition penetrates the soil, for example, nursery tray application, in furrow application, drip irrigation, sprinkler irrigation, soil drenching, soil injection, or incorporation into the soil, and such other methods.

The rates of application or the dosage of the composition depends on the type of use, the type of crops, or the specific active ingredients in the composition but is such that the agrochemical active ingredient, is in an effective amount to provide the desired action (such as nutrient uptake plant vigor, crop yield).

Typically, the agricultural granular composition will not release the nutrient until after application to the desired target. Alternatively, the composition may be designed to release the agrochemical nutrient slowly over a period of time.

Preparation Examples

The following examples illustrate the basic methodology and versatility of the composition of the invention.

TABLE 1

Water dispersible granular Compositions of Algae:

| | Sample Number | | | | | | | | |
|---|---|---|---|---|---|---|---|---|---|
| Constituents | I | II | III | IV | V | VI | VII | VIII | IX |
| *Spirulina Plantensis* | — | 90 | — | 36 | — | 10 | — | — | — |
| *Chlorella pyrenoidosa-* | 50 | — | — | — | — | — | — | — | — |
| Lithothamnium Calcereum | — | — | 60 | — | — | — | — | — | — |
| *Sargassum fusiforme* | — | — | — | — | 10 | — | — | — | 1 |
| *Ascophyllum nodusum* | — | — | — | — | — | 50 | 50 | 40 | — |
| Sulphur | — | — | — | — | 30 | — | — | 40 | — |
| Zinc Oxide | — | — | — | — | 15 | — | — | — | — |
| Naphthalene sulphonate condensate | — | 0.5 | 5 | 3 | 20 | 2 | — | 3 | 15 |
| Sodium Ligno Sulphonate | 30 | 0.409 | 10 | 1 | 23 | — | 1 | 2 | 29 |
| Polyvinyl pyrrolidone | — | — | | 0 | 2 | — | — | — | |
| Maltodextrin | 20 | — | | 0 | — | — | — | — | 40 |
| Starch | — | — | | 0 | — | — | — | — | 15 |
| 1,2-benzoisothiazol-3(2H)-one | — | — | 0.5 | — | — | 0.8 | — | 1 | — |
| Kaolin | — | — | 9.5 | 20 | — | 17.2 | 19 | 10 | — |
| Lactose | — | — | | 20 | — | 10 | 10 | 4 | — |
| Ammonium sulphate | — | — | | 20 | — | — | — | — | — |
| Sodium citrate | — | 9.091 | 15 | — | — | 10 | 20 | — | — |
| Algae:Surfactant or diintegrant or binder ratio | 1:1 | 99:1 | 4:1 | 9:1 | 2:9 | 30:1 | 50:1 | 8:1 | 1:99 |

Sample I was prepared by blending 50 parts of *Chlorella* sp., 30 part of Sodium Ligno Sulphonate and 20 parts of maltodextrin to obtain a blend. The blend obtained was milled to get a powder of less than 10 micron particle size.

The powder was mixed with water in a suitable mixing equipment to form a slurry or wet mix with a solid content of 25% to 75%.

The slurry obtained was wet ground in suitable wet grinding equipment. The wet milled slurry obtained was spray dried at an inlet temperature less than 175° C. and outlet temperature less than 90° C. to get a granular powder with less than 10% moisture. The composition had the following particle size distribution: D10 less than 0.6 microns; D50 less than 4 microns and D90 less than 10 microns. The composition had a dispersibility of 98%, suspensibility of 88% and an angle of repose of 30 degrees.

Samples II-IX were prepared as per the process of preparation of Sample I, wherein the samples included constituents in concentrations as set forth in the above table.

Sample II—

Dispersibility—75%

Initial Suspensibility—74%

Suspensibility on accelerated storage—71.5%

Angle of repose—38 degrees

Sample IX—

Dispersibility—85%

Initial Suspensibility—82%

Suspensibility on accelerated storage—80.5%

Angle of repose—35 degrees

Field Studies:

Field Trial Study of Treatments of *Sargassum* and *Ascophyllum* Compositions against Powdery Mildew on Cucumbers by Foliar Application Field trial was conducted for the evaluation of different treatments at Gandhinagar (Ahemdabad) in Gujarat to evaluate various compositions for treatment of Cucumbers. The plot size was 1048 sqm. Three replications were done. All the recommended agronomic practices were followed. Two sprays of each treatment were applied with the help of knapsack sprayer at 7 days interval.

Percent Disease Index (PDI): It was recorded from 20 plants from each plot per replication on visual basis. The rating scale based on 0, 1, 2, 3, 4 and 5, where 0 was rated for no disease and 5 for >50% disease presence.

$$\text{Percent Disease Index} = \frac{\text{Sum of all disease rating}}{\text{Total no. of rating} \times \text{maximum disease grade}} \times 100$$

TABLE 4

EFFICACY OF VARIOUS TREATMENTS WITH *SARGASSUM* AND *ASCOPHYLLUM* COMPOSITIONS AGAINST POWDERY MILDEW ON CUCUMBERS

| Treatment No. | Composition details | Formulation dosage in gm/ha | Percent Disease Index (PDI) Pre-Spary R1 | R2 | R3 | Mean | 7 DAFS (days after 1st spray) R1 | R2 | R3 | Mean | 7 DASS (days after 2nd spray) R1 | R2 | R3 | Mean | % Disease control |
|---|---|---|---|---|---|---|---|---|---|---|---|---|---|---|---|
| 1 | *Ascophyllum* 90% granule with algae to surfactant or disintegrant or binder ratio of 10:1 (as per embodiment of the invention) | 2778 | 92 | 90 | 91 | 91.0 | 68 | 71 | 67 | 68.7 | 68 | 65 | 61 | 64.7 | 11.6 |
| 2 | Sulphur 40% + *Sargassum* 30% granule with algae to surfactant or disintegrant or binder ratio of 10:1 as per embodiment of the invention | 3000 | 86 | 84 | 90 | 86.7 | 74 | 70 | 65 | 69.7 | 69 | 68 | 62 | 66.3 | 12.2 |
| 3 | *Ascophyllum* Pure powder | 2500 | 85 | 72 | 91 | 82.7 | 80 | 76 | 74 | 76.7 | 76 | 75 | 77 | 76.0 | 7.2 |
| 4 | *Sargassum* pure powder | 900 | 91 | 77 | 93 | 87.0 | 80 | 81 | 79 | 80.0 | 80 | 79 | 79 | 79.3 | 2.9 |
| 5 | Sulphur 80 WG | 1500 | 90 | 86 | 90 | 88.7 | 82 | 79 | 78 | 79.6 | 78 | 75 | 72 | 75.0 | 4.1 |
| 6 | Control | — | 88 | 74 | 90 | 84.0 | 85 | 85 | 88 | 86.0 | 82 | 82 | 87 | 83.7 | 0.0 |

It can be seen from the above table that treatments 1 with water dispersible granular composition of 90% *Ascophyllum* as per the embodiment of the present invention (with ratio of algae to surfactant or disintegrant or binder of 10:1) showed a 11.6% disease control as compared to pure *Ascophyllum* powder which showed 7.2% disease control. Also, water dispersible granular composition of 40% sulphur+30% *Sargassum* as per the embodiment of the present invention (with ratio of algae to surfactant or disintegrant or binder of 10:1) showed a 12.2% control over powdery mildew as compared to pure *Sargassum* powder and sulphur 80 WG which showed only 2.9% and 4.1% control respectively over powdery mildew.

Field Trial Study of Treatments with *Lithothamnium* Compositions on Tomato by Drip Irrigation Field trial was conducted for the evaluation of different treatments at Sabalvad (idar) village to evaluate various compositions of lithothamnium for treatment of Tomato. The plot size was 1028 sqm. All the recommended agronomic practices were followed. Granules of the compositions according to the embodiment (treatment 1) and Calcium nitrate (Green Life) (treatment 3) were applied by drip irrigation. Pure *Lithothamnium* powder could not be added to the drip irrigation system as it settled in the drum and clogged the venture and the nozzles. Hence, it was applied by manual broad casting. Also, no urea or any other chemical fertilizer was applied in the trial and in the previous crop. Thus, the parts where compositions of the present invention were applied were free of chemical nutrient for over a year.

Observations for total plant weight, weight of the fruit and yield were made at the time of harvest.

Plant Weight was recorded from 10 selected plants from each plot per replication. Fruit weight was measured from 10 selected fruits from each plot per replication. Yield was recorded from each plot and converted in to t/acre.

TABLE 5

EFFICACY OF VARIOUS TREATMENTS WITH *LITHOTHAMNIUN* COMPOSITIONS ON TOMATO GROWTH AND YIELD

| | | | | At Harvest | | |
|---|---|---|---|---|---|---|
| Treatment No. | Composition details | Formulation dosage in gm/ha | Calcium dosage gm/ha | Total plant weight (kg/sqm) | 10 Fruit weight (gm) | Yield (t/acre) |
| 1 | *Lithothamnium* 90% granule with algae to surfactant or disintegrant or binder ratio of 18:1 as per embodiment of the invention having 28.5% Calcium | 3300 | 940.5 | 1.71 | 1332 | 49.6 |
| 2 | *Lithothamnium* pure powder having 32% Calcium | 2940 | 940.8 | 1.52 | 1267 | 45.1 |
| 3 | Calcium nitrate (Green Life) having 18.8% Calcium | 5000 | 940 | 1.49 | 1201 | 44.4 |
| 4 | Control | — | — | 1.31 | 1072 | 31.2 |

It can be seen from the above table that treatments 1 with water dispersible granular composition of 90% *Lithothamnion* (having 28.5% Calcium) as per the embodiment of the present invention (with ratio of algae to surfactant or disintegrant or binder of 18:1) at the dosage of 3300 gm/ha showed 14.8% increase in the total plant weight and 11.7% increase in the total crop yield as compared to Treatment 3 with a commercially available calcium based product, Green life (having 18.8% Calcium) at the dosage of 5000 gm/ha, as well as 12.5% increase in the total plant weight and 9.97% increase in the total crop yield as compared to Treatment 2 with pure *Lithothamnium* powder (having 32% calcium) at the dosage of 2940 gm/ha. The composition of treatment 1 also showed a significant increase in the fruit weight as compared to the commercially available composition. The results in the yield enhancement are particularly surprising as the amount of calcium applied in each treatment were same i.e. around 940 gm/ha.

Field Trial Study of Treatments with *Chlorella* Compositions on Maize by Drip Irrigation.

Trials were laid in Choriwad (Idar) village, Dist.-Sabarkantha, Gujarat, India, to evaluate various compositions for treatment of Maize Hightech variety (Sona company). The plot size was 3828 m2. All the recommended agronomic practices were followed. Granules of the compositions according to the embodiment (treatment 1) and water soluble fertilizer (WSF 9-19-19, treatment 3) were applied by drip irrigation. Pure *Chlorella* powder could not be added to the drip irrigation system as it settled in the drum and clogged the venture and the nozzles, hence it was applied by manual broadcasting. Also, no urea or any other chemical fertilizer was applied in the trial and in the previous crop. Thus, the parts where compositions of the present invention were applied were free of chemical nutrient for over a year.

Observations for plant height, yield and nutrient uptake for the trials are shown below. Assessments were made as follows:

Plant Height was recorded from 10 selected plants from each plot per replication. Grain yield was recorded from one sqm area from each plot per replication and converted in to q/ha.

TABLE 6

EFFICACY OF VARIOUS TREATMENTS WITH *CHLORELLA* COMPOSITIONS ON MAIZE GROWTH AND YIELD

| Treatment | | Formulation dosage in | Plant height (cm)* | | | Grain yield/ha |
|---|---|---|---|---|---|---|
| No. | Composition details | gm/ha | 30 DAA | 60 DAA | 90 DAA | (in Qtl) |
| 1. | *Chlorella* 50% granule with algae to surfactant or disintegrant or binder ratio of 5:4 as per embodiment of the invention | 6000 | 199.8 | 230.03 | 257.07 | 144.68 |
| 2. | *Chlorella* pure powder | 3000 | 196.53 | 227.8 | 253.6 | 136.6 |
| 3. | WSF (19-19-19) (commercial N—P—K fertilizer with 19% of N, P and K each) | 7500 | 196.33 | 226.43 | 252.97 | 135.45 |
| 4. | Control | — | 190.33 | 219.23 | 246.53 | 127.55 |

It can be seen from the above table that treatment 1 with water dispersible granular composition of 50% *Chlorella* as per the embodiment of the present invention (with ratio of algae to surfactant or disintegrant or binder of 5:4) showed a significant increase in plant height on 30, 60 and 90 days after treatment as compared to treatments 2 and 3 with *Chlorella* pure powder, and WSF (19-19-19) (commercial N-P-K fertilizer with 19% of N, P and K each) respectively. Also, water dispersible granules prepared as per the embodiment of the present invention surprisingly showed yield improvement of 5.9% and 6.8% as compared to treatments 2 and 3 with *Chlorella* powder and WSF (19-19-19) (commercial N-P-K fertilizer) respectively. Treatment 1 also gave a 13.4% higher yield over untreated control.

TABLE 7

EFFICACY OF VARIOUS TREATMENTS OF *CHLORELLA* COMPOSITIONS ON MAIZE WITH RESPECT TO NUTRIENT UPTAKE

| | | | Soil Sample | | | | | | | | |
|---|---|---|---|---|---|---|---|---|---|---|---|
| | | Formulation | Available Nitrogen (kg/ha) | | | Available Phosphorus (kg/ha) | | | Available Potash (kg/ha) | | |
| Treatment No. | Composition details | dosage in gm/ha | DBA | 30 DAA | 90 DAA | DBA | 30 DAA | 90 DAA | DBA | 30 DAA | 90 DAA |
| 1. | *Chlorella* 50% granule with algae to surfactant or disintegrant or binder ratio of 5:4 as per embodiment of the invention | 6000 | 1004 | 942 | 734 | 87.56 | 68.64 | 47.41 | 243 | 181 | 74 |
| 2. | *Chlorella* pure powder | 3000 | | 974 | 912 | | 73.94 | 69.64 | | 202 | 154 |
| 4. | WSF (19-19-19) (commercial N—P—K fertilizer with 19% of N, P and K each) | 7500 | | 987 | 903 | | 82.28 | 72.45 | | 214 | 183 |
| 5. | Control | — | | 996 | 974 | | 85.32 | 80.92 | | 223 | 209 |

The uptake of nitrogen, phosphorus and potash were recorded before application and 30th and 90th days after application. From the above table, it has been observed that treatment 1 (with *Chlorella* 50% granule with algae to surfactant or disintegrant or binder ratio of 5:4 as per embodiment of the invention) recorded minimum nitrogen in soil which indicates highest nitrogen uptake by plant. The maximum soil nitrogen was recorded in untreated crop which indicated the low nitrogen uptake by plant. In case of phosphorus and potash uptake also, it was observed that treatment 1 (with *Chlorella* 50% granule with algae to surfactant or disintegrant or binder ratio of 5:4 as per embodiment of the invention) recorded highest uptake followed by the treatment 2 (*Chlorella* pure powder), treatment 3 (WSF (19-19-19) commercial N-P-K fertilizer with 19% of N, P and K each) and untreated crop recorded minimum phosphorus and potash uptake.

As mentioned above no urea or any other chemical fertilizer was applied in the trial and in the previous crop. Hence, it is surprising to note the uptake of nutrients from the soil with the composition of the present embodiment, despite no application of chemical fertilizers.

Field Trial Study of Treatments with *Spirulina* Compositions on Groundnut by Soil Drenching.

Trials were laid in Ishvarpura (Idar) village, Dist.-Sabarkantha, Gujarat, India, to evaluate various compositions for treatment of Groundnut GG-2 variety. The plot size was 3828 m2. All the recommended agronomic practices were followed. All the treatments were applied by Soil drenching. Also, no urea or any other chemical fertilizer was applied in the trial and in the previous crop. Thus, the parts where compositions of the present invention were applied were free of chemical nutrient for over a year.

TABLE 8

EFFICACY OF VARIOUS TREATMENTS WITH SPIRULINA COMPOSITIONS ON GROUNDNUT WITH RESPECT TO YIELD

| Treatment No. | Composition details | Formulation dosage in gm/ha | Grain yield/ha (in Qtl) |
|---|---|---|---|
| 1. | Spirulina 50% WG with ratio of algae to surfactant or disintegrant or binder of 5:4 (as per the embodiment of the present invention) | 3000 | 3212.5 |
| 2. | Spirulina 30% + Urea 30% granule with algae to surfactant or disintegrant or binder ratio of 3:1 (as per embodiment of the invention) | 5000 | 3326.5 |
| 3. | Spirulina 20% + Sulphur 60% granule with algae to surfactant or disintegrant or binder ratio of 1:1 (as per embodiment of the invention) | 5000 | 3348.5 |
| 4. | Spirulina Pure powder | 1500 | 2567.5 |
| 5. | Sulphur 90% WG | 7500 | 3010 |

TABLE 8-continued

EFFICACY OF VARIOUS TREATMENTS WITH SPIRULINA COMPOSITIONS ON GROUNDNUT WITH RESPECT TO YIELD

| Treatment No. | Composition details | Formulation dosage in gm/ha | Grain yield/ha (in Qtl) |
|---|---|---|---|
| 6. | Urea | 230000 | 2467.5 |
| 7. | WSF (19-19-19) (commercial N-P-K fertilizer with 19% of N, P and K each) | 7500 | 2427.5 |
| 8. | Control | — | 2117.5 |

It can be seen from the above table that treatments 1 with water dispersible granular composition of 50% *Spirulina* as per the embodiment of the present invention (with ratio of algae to surfactant or disintegrant or binder of 5:4) showed a 25.12% increase in grain yield as compared to *Spirulina* pure powder. Also, *Spirulina* 30%+Urea 30% granule with algae to surfactant or disintegrant or binder ratio of 3:1 (as per embodiment of the invention) showed 34.8% and 37% increase in grain yield as compared to plain urea and WSF (19-19-19) (commercial N-P-K fertilizer with 19% of N, P and K each) respectively. Further, *Spirulina* 20%+Sulphur 60% granule with algae to surfactant or disintegrant or binder ratio of 1:1 (as per embodiment of the invention) showed 11.2% and 30.4% increase in grain yield as compared to Suphur 90% WG and *Spirulina* pure powder respectively. The compositions of the present invention also enable the farmers to reduce dosage of synthetic chemical fertilizers and optimize plant health and yields.

TABLE 9

EFFICACY OF VARIOUS TREATMENTS WITH SPIRULINA COMPOSITIONS ON GROUNDNUT WITH RESPECT TO NUTRIENT UPTAKE

| Treatment No. | Composition details | Formulation dosage in gm/ha | Protein content of Groundnut Seeds % |
|---|---|---|---|
| 1. | Spirulina 30% + Urea 30% granule with algae to surfactant or disintegrant or binder ratio of 3:1 (as per embodiment of the invention) | 5000 | 55.216% |

TABLE 9-continued

EFFICACY OF VARIOUS TREATMENTS WITH SPIRULINA COMPOSITIONS ON GROUNDNUT WITH RESPECT TO NUTRIENT UPTAKE

| Treatment No. | Composition details | Formulation dosage in gm/ha | Protein content of Groundnut Seeds % |
|---|---|---|---|
| 2. | Urea | 230000 | 48.884% |
| 3. | WSF (19-19-19) (commercial N-P-K fertilizer with 19% of N, P and K each) | 7500 | 49.349% |
| 4. | Control | — | 47.208% |

It can be seen from the above table that treatments 1 with water dispersible granular composition of 30% *Spirulina*+30% Urea as per the embodiment of the present invention (with ratio of algae to surfactant or disintegrant or binder of 3:1) show improved protein content as compared to treatments 2 and 3 with plain urea and WSF (19-19-19) (commercial N-P-K fertilizer with 19% of N, P and K each).

Field Trial Study on Chilli by Soil Application against Nematodes.

Trials were laid in Sabalvad (Idar) village, Gujarat, India, to evaluate various compositions against nematodes in Chilly. All the recommended agronomic practices were followed. All the treatments were applied by Soil application.

Percent Disease Index (PDI): It was recorded from 20 plants from each plot per replication on visual basis. The rating scale based on 0, 1, 2, 3, 4 and 5, where 0 was rated for no gall on roots and 5 for >50% gall on roots.

$$\text{Percent Disease Index} = \frac{\text{Sum of all rating}}{\text{Total no. of rating} \times \text{maximum grade}} \times 100$$

TABLE 10

EFFICACY OF VARIOUS TREATMENTS WITH *SPIRULINA* COMPOSITIONS ON CHILLY AGAINST NEMATODE

| Treatment No. | Composition details | Formulation dosage in gm/ha | Active/s dosage gm/ha | PDI at 30 DAA R1 | R2 | R3 | Mean | PDI at 60 DAA R1 | R2 | R3 | Mean | % control |
|---|---|---|---|---|---|---|---|---|---|---|---|---|
| 1. | *Spirulina* 15% + *Bacillus firmus* 20% granule with algae to surfactant or disintegrant or binder ratio of 1:1 (as per embodiment of the invention) | 3000 | 450 + 600 | 29 | 26 | 35 | 30 | 51 | 38 | 30 | 39.67 | 56.82 |
| 2. | *Spirulina* Pure powder | 450 | 450 | 48 | 44 | 48 | 46.7 | 99 | 95 | 100 | 98 | 10.33 |
| 3. | 1% *Bacillus firmus* wettable powder | 60000 | 600 | 44 | 28 | 36 | 36 | 80 | 45 | 60 | 61.67 | 39.46 |
| 4. | Control | — | — | 62 | 70 | 52 | 61.3 | 100 | 100 | 100 | 100 | 0.00 |

Composition of *Spirulina* 15%+*Bacillus Firmus* 20% was made by extrusion. *Spirulina* and the excipient were blended and milled in an air mill to get a desired particle size of 0.1 microns to 15 microns. Water, spores of *Bacillus firmus* were added to the milled mixture and extruded through a low pressure extruder and the granules formed were dried in a post fluid bed dryer.

It can be seen from the above table that treatment 1 with water dispersible granular composition of *Spirulina* 15%+ *Bacillus firmus* 20% as per the embodiment of the present invention (with ratio of algae to surfactant or disintegrant or binder of 1:1) showed 56.82% nematode control whereas pure *Spirulina* powder showed only 10.33% nematode control and commercial product 1% *Bacillus firmus* wettable powder showed only 39.46% nematode control.

Thus, it has been observed that the composition of the present invention, demonstrates enhanced, efficacious and superior behaviour in the fields. In fact, various advantageous properties associated with the compositions according to the invention, include but are not limited to advantageous behavior during formulating and/or upon application, improved stability, improved toxicological and/or ecotoxicological behaviour, improved crop characteristics including crop yields, crop qualities such as improved nutrient content, more developed root system, increase in plant height, bigger leaf blade, less dead basal leaves, stronger tillers, greener leaf color, less fertilizers needed, tillering increase, increased shoot growth, improved plant vigor, earlier flowering, more productive tillers, less plant verse (lodging), improved chlorophyll content of the leaves, protein content, photosynthetic activity, early seed germination, early grain maturity, improved quality of the produce, increased plant, improved fortification of the plant, conditioning the soil and other advantages familiar to a person skilled in the art. Also, the compositions of the inventions are also suitable for drip irrigation or sprinkler irrigation in addition to other methods of applications of the agricultural compositions, in which most of the commercial products and prior art products fail.

Through the composition of the present invention, the number of applications or the amount of nutrients, fertilizers or pesticides are minimized. The composition is highly safe to the user and to the environment. The composition is also cost-effective, as it provides much greater simultaneous control and it is used in a variety of crops with a broader spectrum of protection. Also, the compositions serve as an intervention application between very specific actives, which are likely to lead to resistance in areas of epidemic and high frequency of pesticidal/fertilizer applications, saves labour costs and minimizes the use of chemical fertilizers b farmers and at the same time are also cost effective.

From the foregoing it will be observed that numerous modifications and variations can be effectuated without departing from the true spirit and scope of the novel concepts of the present invention. It is to be understood that no limitation with respect to the specific embodiments illustrated is intended or should be inferred.

I claim:

1. A water dispersible granular composition comprising at least one algae and at least one of agrochemical excipient comprising at least one or more of surfactant, binder or disintegrant wherein, the weight ratio of algae to at least one of surfactant, binder or disintegrant is 99:1 to 1:99 wherein the algae comprises 0.1% to 90% by weight of the total composition, and wherein the composition has a particle size in the range of 0.1 microns to 60 microns.

2. The water dispersible granular composition of claim 1, wherein the weight ratio of algae to at least one of surfactant, binder or disintegrant is 99:1 to 1:50.

3. The water dispersible granular composition of claim 1, wherein the algae comprise one or more of green algae, red algae, golden algae, brown algae, golden-brown algae, blue algae, blue-green algae or derivatives, species and mixtures thereof.

4. The water dispersible granular composition of claim 1, wherein the algae comprises one or more of Cyanobacteria, Ochrophytes, Glaucophytes, Rhodoplasts, Rhodophytes, Chloroplasts, Chrysophyta, Synurophytes, Silicoflagellata, Heterokonts, Crytophytes, Haptophytes, Euglenophytes, Chlorophytes, Charophytes, Embrophyta Or Chlorarachniophytes or derivatives, species and mixtures thereof.

5. The water dispersible granular composition of claim 1, wherein the algae comprises at least one of *Spirulina* Sp., *Arthrospira* Sp., *Chlorella* Sp., *Anabaena* Sp., *Sargassum* Sp., *Scenedesmus* Sp., *Aphanizomenon* Sp., *Dunaliella* Sp., *Phymatolithion* Sp., *Lithothamnium* Sp., *Ascophyllum* Sp., *Enteromorpha* Sp., *Tetraselmis* Sp., *Prymnesium* Sp., *Chlamydomonas* Sp., *Euglena* Sp., *Caulerpa* Sp., *Padina* Sp., *Urophora* Sp., *Chondria* Sp., *Caulerpa* Sp., *Lyngby* Sp., *Prasiola* Sp., *Gymnopilus* Sp., *Melanothamnus* Sp., *Turbeneria* Sp., *Mastigocladopsis* Sp., *Hydroclathrus* Sp., *Cystoseira* Sp., *Laminaria* Sp., *Fucus* Sp., *Ulva* Sp. or derivatives and mixtures thereof.

6. The water dispersible granular composition of claim 1, wherein the composition comprises one or more of fillers or carriers or diluents, spreading agents, pigments, colorants, buffers or pH adjusters or neutralizing agents, antifoaming agents or defoamers, anti-settling agents, penetrants, preservatives, ultraviolet absorbents, UV ray scattering agents, stabilizers, and mixtures thereof.

7. The water dispersible granular composition of claim 1, wherein the agrochemically acceptable excipient is in the range of 0.1% to 99.9% by weight of the total composition.

8. The water dispersible granular composition of claim 1, wherein the granular composition has dispersibility of at least 50%.

9. The water dispersible granular composition of claim 1, wherein the composition has an initial suspensibility of at least 50%.

10. The water dispersible granular composition of claim 1, wherein the composition has angle of repose in the range of 25 degrees to 40 degrees.

11. The water dispersible granular composition of claim 1, wherein the composition has a wettability of less than 5 minutes.

12. The water dispersible granular composition of claim 1, wherein the composition further comprises at least one of microbes, pesticidal actives, nutrients, fertilizers or mixtures thereof.

13. The water dispersible granular composition of claim 12, wherein the microbe is *Bacillus* spp.

14. The water dispersible granular composition of claim 12, wherein the fertilizer comprises elemental sulphur or urea.

15. A process of preparation of the water dispersible granular composition comprising at least one algae and at least one agrochemically acceptable excipient comprising at least one of surfactant, binder or disintegrant wherein the weight ratio of algae to at least one of surfactant, binder or disintegrant is 99:1 to 1:99 wherein the algae comprises 0.1% to 90% by weight of the total composition, and wherein the process comprises:

a. Milling a blend of at least one algae and at least one agrochemically acceptable excipient to obtain a slurry or wet mix;

b. Drying the wet mix to obtain the water dispersible granular composition with a particle size of 0.1 microns to 60 microns.

16. The water dispersible granular composition as claimed in claim 1 which is a fertilizer composition, a nutrient composition, a plant strengthener composition, a soil conditioner composition, a yield enhancer composition or a plant protection composition.

17. A method of protection of plant or improving its health or yield, the said method comprising treating at least one of a plant, a plant propagation material, locus or parts thereof, a seed, seedling or surrounding soil with the water dispersible agricultural granular composition comprising: at least one algae and at least one agrochemically acceptable excipient comprising at least one of surfactant, binder or disintegrant wherein the weight ratio of algae to at least one of surfactant, binder or disintegrant is 99:1 to 1:99 wherein the algae comprises 0.1% to 90% by weight of the total composition.

* * * * *